United States Patent [19]

Itoh et al.

[11] 4,250,246

[45] Feb. 10, 1981

[54] PHOTOGRAPHIC LIGHT-SENSITIVE SHEET FOR THE COLOR DIFFUSION TRANSFER PROCESS

[75] Inventors: Isamu Itoh; Yoshinobu Yoshida, both of Minami-ashigara, Japan

[73] Assignee: Fuji Photo Film Co., Ltd., Minami-ashigara, Japan

[21] Appl. No.: 51,585

[22] Filed: Jun. 25, 1979

[30] Foreign Application Priority Data

Jun. 23, 1978 [JP] Japan .................................. 53-76162

[51] Int. Cl.$^3$ .......................... G03C 1/40; G03C 7/00
[52] U.S. Cl. .................................... 430/223; 430/242; 430/562; 430/958
[58] Field of Search ................ 430/223, 242, 562, 958

[56] References Cited

U.S. PATENT DOCUMENTS

| | | | |
|---|---|---|---|
| 3,954,476 | 5/1976 | Krutak et al. | 430/223 |
| 4,135,929 | 1/1979 | Fernandez et al. | 430/223 |
| 4,139,383 | 2/1979 | Odenwalder et al. | 430/242 |
| 4,156,609 | 5/1979 | Landholm et al. | 430/223 |

*Primary Examiner*—J. Travis Brown
*Attorney, Agent, or Firm*—Sughrue, Rothwell, Mion, Zinn and Macpeak

[57] ABSTRACT

A photographic light-sensitive sheet for the color diffusion transfer process which comprises a support having thereon at least one light-sensitive silver halide emulsion layer having associated therewith a magenta dye releasing redox (DRR) compound.

13 Claims, No Drawings

PHOTOGRAPHIC LIGHT-SENSITIVE SHEET FOR THE COLOR DIFFUSION TRANSFER PROCESS

BACKGROUND OF THE INVENTION

1. Field of the Invention

The present invention relates to a photographic light-sensitive sheet for the color diffusion transfer process and, more particularly, to a silver halide photographic light-sensitive sheet for the color diffusion transfer process containing a novel dye releasing redox (DDR) compound.

2. Description of the Prior Art

Color diffusion transfer color image forming processes using a dye releasing redox compound are described in Japanese Patent Application (OPI) Nos. 33826/73 (The term "OPI" as used herein refers to a "published unexamined Japanese patent application"), 114424/74, 126331/74, 126332/74, 115528/75 and 104343/76, U.S. Pat. Nos. 3,928,312, 3,931,144 and 3,954,476 and Research Disclosure, No. 13024 (1975), ibid., No. 16475 (1977). The term "dye releasing redox compound" means a compound containing therein a redox moiety and a dye moiety (including a precursor thereof). The redox moiety renders the redox compound immobile due to a ballast group attached thereto, but upon redox reaction under alkaline conditions the comound per se splits and releases a compound having the dye moiety (a dye compound). That is, when a light-sensitive element having a light-sensitive silver halide emulsion layer and a dye-releasing redox compound associated therewith is exposed and developed with an alkaline processing solution, the redox compound per se is oxidized in proportion to the amount of developed silver halide and the compound splits into a compound containing the dye moiety and a nondiffusible compound in the alkaline processing solution. As a result, the compound containing the dye moiety diffuses into an image-receiving layer to provide a transferred image therein.

Examples of dye-releasing redox compounds which release magenta dyes are described in Japanese Patent Application (OPI) Nos. 115528/75 and 114424/74, U.S. Pat. Nos. 3,932,380 and 3,931,144, etc. However, technical problems are encountered using these magenta dye releasing redox compounds specifically described in such prior art in that the transferred images have insufficient stability. For example, the light fastness of the images is not adequate and the images fade to a large extent even in a dark place. Also, the transfer of the dye compound is not adequate.

For instance, with respect to the fading-in-dark of transferred dye images, it has been known that unreacted monomer (such as acrylic acid, butyl acrylate, etc.) in the neutralizing layer containing a polymer acid such as polyacrylic acid, a copolymer of acrylic acid and butyl acrylate, etc., as disclosed in U.S. Pat. No. 3,362,819 hereinafter described, adversely influences the fading-in-dark of transferred dye images. It has also been found upon further investigation that unreacted butyl acrylate monomer exceptionally degrades the fading-in-dark of magenta dye images obtained from prior art dye-releasing redox compounds such as described in U.S. Pat. No. 3,932,380. However, it is extremely difficult from a technical standpoint to limit the amount of unreacted monomer during the synthesis of polymer acid for a neutralizing layer to an extent that does not adversely influence thelight fastness of the images. Therefore, it has been desired to develop a redox compound which releases a dye compound which is less susceptible to such a monomer.

SUMMARY OF THE INVENTION

A first object of the present invention is to provide a dye-releasing redox compound which provides a stable magenta dye image.

A second object of the present invention is to provide a dye-releasing redox compound having a dye moiety whose color hue is excellent.

A third object of the present invention is to provide a dye-releasing redox compound which provides a transferred dye image which does not change hue with pH.

A fourth object of the present invention is to provide a photographic light-sensitive sheet for the color diffusion transfer process containing a dye-releasing redox compound which provides a transferred magenta dye image having a sufficiently high optical density in the presence of a relatively small amount of silver halide.

A fifth object of the present invention is to provide a photographic light-sensitive sheet for the color diffusion transfer process in which a light-sensitive element is also utilized as a negative film.

The inventors have conducted various investigations and found that the above-described objects are effectively attained by a photographic light-sensitive sheet with satisfactory photographic properties for the color diffusion transfer process which contains a dye-releasing redox compound represented by the following general formula (I):

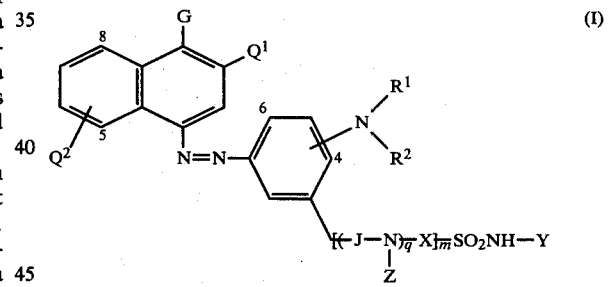

wherein $Q^1$ represents a hydrogen atom, a halogen atom, a sulfamoyl group represented by the formula $-SO_2NR^3R^4$ wherein $R^3$ represents a hydrogen atom or an alkyl group; $R^4$ represents a hydrogen atom or an $R^{4a}$ group wherein $R^{4a}$ represents an alkyl group, an aralkyl group or a phenyl group; and $R^3$ and $R^4$ may combine directly or through an oxygen atom to form a ring; a group represented by the formula $-SO_2R^5$ wherein $R^5$ represents an alkyl group, or an aralkyl group; a carboxy group, a group represented by the formula $-COOR^6$ wherein $R^6$ represents an alkyl group, or a phenyl group; or a group represented by the formula $-CONR^3R^4$ wherein $R^3$ and $R^4$ each has the same meaning as defined above; $Q^2$ is positioned at the 5- or the 8-position to the hydroxy group and represents a hydroxy group, a group represented by the formula $-NHCOR^{4a}$ or a group represented by the formula $-NHSO_2R^{4a}$ wherein $R^{4a}$ has the same meaning as defined above; G represents a hydroxyl group, a salt thereof, or a hydrolyzable acyloxy group represented by the formula

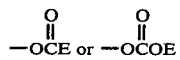

wherein E represents an alkyl group or a phenyl group; $R^1$ and $R^2$, which may be the same or different each represents an alkyl group; and $R^1$ and $R^2$ may combine with each other and represent an atomic group necessary to form a 5-membered or 6-membered heterocyclic ring; m and q each represents 0 or 1; J represents a sulfonyl group or a carbonyl group; Z represents a hydrogen atom or an alkyl group; X represents a divalent bonding group represented by the formula $-A^1-L_n(A^2)_p$ wherein $A^1$ and $A^2$, which may be the same or different each represents an akylene group, an aralkylene group, a phenylene group or a substituted phenylene group; L represents a divalent group selected from an oxy group, a carbonyl group, a carboxyamido group, a carbamoyl group, a sulfonamido group, a sulfamoyl group, a sulfinyl group and a sulfonyl group, and p and n each represents 0 to 1; and the group represented by the formula $Y-NHSO_2-$ is a redox center which functions to release a diffusible dye as a result of self cleavage due to oxidation.

DETAILED DESCRIPTION OF THE INVENTION

In the above-description general formula (I), the compound is characterized by the presence of the substituted amino group $-NR^1R^2$. Due to the presence of the substituted amino group, a transferred magenta dye image having an excellent color hue is obtained and in addition the fading-in-light and the fading-in-dark of the transferred image are markedly improved and thus the durability of color images both in a light place and in dark place is extremely improved. In this connection, the effects of the amino group $-NR^1R^2$ are neither known nor suggested in the above-described prior art.

The magenta dye releasing redox compound according to the present invention is described in greater detail below.

The amino group $-NR^1R^2$ is preferably positioned at the 4-position or the 6-position with respect to the azo group.

The alkyl group represented by $R^1$ and $R^2$ can be a straight chain, branched chain or cyclic alkyl group and includes substituted alkyl groups. Preferred examples includes an alkyl group having 1 to 6 carbon atoms, more preferably 1 to 4 carbon atoms (e.g., a methyl group, an ethyl group, an n-propyl group, an isopropyl group, an n-butyl group, a cyclohexyl group, etc.), a substituted alkyl group having 1 to 10 carbon atoms, more preferably 1 to 5 carbon atoms substituted with an alkoxy group, an alkoxyalkoxy group or a halogen atom, etc. (e.g., a methoxyethoxyethyl group, methoxyethyl group, a chloroethyl group, etc.), and the like.

Further, the atomic groups necessary to form a 5-membered or 6-membered heterocyclic ring by connecting $R^1$ and $R^2$ include carbon atom chains such as an alkylene chain of 4 to 6 carbon atoms (e.g., an alkylene chain capable of forming a 5- or 6-membered ring together with the nitrogen atom such as $-(CH_2)_4-$, $-(CH_2)_5-$, $-CH_2CH_2CH_2CH_2CH(CH_3)-$, $-CH_2CH_2CH_2CH(CH_3)CH_2-$ or $-CH_2CH_2CH(CH_3)CH_2CH_2-$) and carbon atom chains including an oxygen atom such as $-CH_2CH_2-O-CH_2CH_2-$ or $-CH_2CH(CH_3)-O-CH(CH_3)CH_2-$.

In the sulfamoyl group represented by the formula $-SO_2NR^3R^4$, $R^3$ is preferably a hydrogen atom, an alkyl group having 1 to 8 carbon atoms, more preferably 1 to 4 carbon atoms including substituted alkyl groups having 1 to 8 carbon atoms, more preferably 1 to 4 carbon atoms in the alkyl moiety. $R^4$ is preferably a hydrogen atom, a straight chain, branched chain or cyclic alkyl group having 1 to 8 carbon atoms, more preferably 1 to 4 carbon atoms, a substituted alkyl group having 1 to 8 carbon atoms, more preferably 1 to 4 carbon atoms in the alkyl moiety, a monocyclic aralkyl group having 7 to 9 carbon atoms (e.g., a phenethyl group, a benzyl group, etc.), a phenyl group including a substituted phenyl group having 6 to 9 carbon atoms. Also $R^3$ and $R^4$ may be combined directly or through an oxygen atom to form a 5- to 6-membered ring.

The cases where: (1) $R^3$ and $R^4$ each represents a hydrogen atom and (2) one of $R^3$ and $R^4$ represents a hydrogen atom and the other of $R^3$ and $R^4$ represents an alkyl group having 1 to 4 carbon atoms, are particularly preferred due to the ready availability of their starting materials and the excellent transferability of the dye compound formed. The same is true for the $-CONR^3R^4$ group.

With respect to the $-SO_2R^5$ group, $R^5$ preferably represents a straight chain, branched chain or cyclic alkyl group (including substituted alkyl groups) having 1 to 8 carbon atoms in the alkyl moiety, or a monocyclic aralkyl group having 7 to 9 carbon atoms (e.g., a phenethyl group, a benzyl group, etc.). In particular, an alkyl group having 1 to 4 carbon atoms and a benzyl group are preferred due to the ready availability of the starting materials and excellent transferability of the dye compound formed.

In case of the $-COOR^6$ group, $R^6$ preferably represents a straight chain, branched chain or cyclic alkyl group having 1 to 8 carbon atoms, more preferably 1 to 4 carbon atoms including a substituted akyl group having 1 to 8 carbon atoms, more preferably 1 to 4 carbon atoms in the alkyl moiety, a phenyl group including a substituted phenyl group having 6 to 9 carbon atoms.

Examples of suitable substituents making up the above-described substituted alkyl groups represented by $R^3$ to $R^6$ include one or more of a cyano group, a methoxy group, an ethoxy group, an alkoxyalkoxy group having 3 to 5 carbon atoms (e.g., a methoxymethoxy group, an ethoxyethoxy group, etc.), a hydroxy group, a carboxy group, a sulfo group, etc. Further, examples of suitable substituents which can be present in the above-described substituted phenyl group represented by $R^3$ and $R^6$ include a method group, a hydroxy group, a halogen atom (e.g., fluorine, chlorine, etc.), a carboxy group, a sulfo group, a sulfamoyl group (e.g., an aminosulfonyl group, a dimethylaminosulfonyl group, etc.), etc.

Examples of G include a hydroxy group or a salt thereof such as an alkali metal salt (e.g., $-O^-Li^+$, $-O^-K^+$ or $-O^-Na^+$) or a photographically inert ammonium salt (e.g., $-O^-NH_4{}^+$, $-O^-NH(CH_3)_3{}^{+l}$, $-O^-N(C_2H_5)_4{}^+$, etc.). G also represents a hydrolyzable acyloxy group represented by the formula

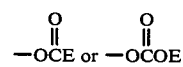

wherein E represents an alkyl group which can be a straight chain, branched chain or cyclic alkyl group and have 1 to 8 carbon atoms (e.g., a methyl group, an ethyl group, an isopropyl group, a cyclohexyl group, etc.), a substituted alkyl group, for example, having 1 to 6 carbon atoms in the alkyl moiety, a phenyl group or a substituted phenyl group.

Examples of suitable substituents making up the above-described substituted alkyl groups represented by E include one or more of a hydroxy group, a carboxy group, a cyano group, an alkoxy group (e.g., having 1 to 3 carbon atoms), a halogen atom (e.g., fluorine, chlorine, etc.), etc.

Examples of suitable substituents making up the above-described substituted phenyl groups represented by E include a cyano group, a halogen atom (e.g., fluorine, chlorine, etc.), a carboxy group, a sulfo group, a nitro group, etc.

Examples of suitable hydrolyzable acyloxy groups are, for example, acetate, chloroacetate, 2-chloroethylcarbonate, phenylcarbonate, 4-chlorobenzoate, 2,5-dichlorobenzoate, 4-nitrobenzoate, 3,5-dinitrobenzoate, etc., but should not be limited thereto.

J represents a sulfonyl group or a carbonyl group, and preferably a sulfonyl group.

Z represents a hydrogen atom, a straight chain alkyl group having 1 to 3 carbon atoms (e.g., a methyl group, an ethyl group, a propyl group, etc.), or a substituted alkyl group having 1 to 3 carbon atoms in the alkyl moiety (substituted with a hydroxy group, a methoxy group, etc.), and preferably a hydrogen atom.

As the substituted phenylene group represented by $A^1$ or $A^2$, those groups having a total of 6 to about 9 carbon atoms are preferred. Examples of the substituents include a methoxy group, an ethoxy group, a straight chain alkoxyalkoxy group having 3 to 4 carbon atoms (e.g., a methoxyethoxy group, an ethoxyethoxy group, etc.), a straight chain alkyl group having 1 to 3 carbon atoms (e.g., a methyl group, an ethyl group, an isopropyl group, etc.), a halogen atom (e.g., fluorine, chlorine, etc.), etc. Of alkylene groups for $A^1$ or $A^2$, those groups having 2 to about 4 total carbon atoms are preferred such as $-(CH_2)_2-$ or $-(CH_2)_4-$. Of aralkylene groups for $A^1$ or $A^2$, those groups having 7 to about 8 total carbon atoms are preferred such as

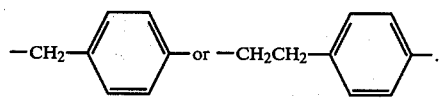

Preferred divalent groups for L are an oxy group and a sulfo group.

Of the dye-releasing redox compounds according to the present invention, those represented by the general formula (I) wherein n=1 and p=0 are preferred, and those represented by the general formula (I) wherein q=0, m=1 and Y—NHSO$_2$—X— is a Y—NHSO$_2$—(alkylene)—SO$_2$— group, a Y—NHSO$_2$—C$_6$H$_4$CH$_2$SO$_2$— group or a Y—NHSO$_2$-(substituted or unsubstituted phenylene)—SO$_2$— group are more preferable. From the standpoint of the diffusibility of released dyes those in which m=0 are particularly preferred.

Examples of Y include a carboxyclic ring having at least one unsaturated double bond and a ballast group, and a hydroxy group or a precursor thereof (a group capable of providing an OH group by hydrolysis), an amino group including a substituted amino group (an amino group substituted with an alkyl group, an aryl group, an acyl group, etc.) is bonded at the o-position or p-position with respect to the —SO$_2$NH— group connected to the unsaturated double bond. The carbocyclic ring may be condensed with a saturated or unsaturated hydrocarbon ring which may be, for example, 5-membered or 6-membered ring such as a benzene ring and a saturated or unsaturated heterocyclic ring which may be, for example, 5-membered or 6-membered. Examples of Y also include a 5- or 6-membered heterocyclic ring such as a pyrrole or indole ring having a ballast group and bonded with an —SO$_2$NH— group at the 3-position thereof.

Examples of those Y—NHSO$_2$— groups are described in U.S. Pat. Nos. 4,055,428 and 3,928,312, French Pat. No. 2,284,140, German Patent Application (OLS) Nos. 2,505,248 and 2,645,656, Japanese Patent Application (OPI) Nos. 3819/78 and 50736/78, etc.

As the redox center represented by Y—NHSO$_2$—, a sulfamoyl group substituted with an o- or p-hydroxyaryl group having a ballast group is preferred. The group represented by the following general formula (II) is particularly preferred as the redox center.

wherein Ball represents a ballast group; T represents an atomic group necessary to complete a benzene ring including a substituted benzene ring or a naphthalene ring including a substituted naphthalene ring; the —NHSO$_2$— group is present at the o- or p-position to the hydroxy group; and when T represents the atoms necessary to complete a naphthalene ring, Ball can be bonded to either of the two rings.

Examples of suitable substituents which can be present on the benzene ring or the naphthalene ring include, for example, straight chain, branched chain or cyclic alkyl group (preferably an alkyl group having 1 to 8 carbon atoms), a straight chain, branched chain or cyclic alkoxy group (preferably having 1 to 8 carbon atoms), a halogen atom (such as a chlorine atom, etc.), etc., or a saturated ring fused to the benzene ring.

The ballast group is an organic ballast group capable of rendering the dye-releasing redox compound non-diffusible during development in an alkaline processing solution and preferably is or contains a hydrophobic residue having 8 to 32 carbon atoms. This organic ballast group can be bonded to the dye-releasing redox compound directly or through a linking group, for example, an imino bond, an ether bond, a thioether bond, a carbonamido bond, a sulfonamido bond, a ureido bond, an ester bond, an imido bond, a carbamoyl bond, a sulfamoyl bond, etc., alone or in combination thereof.

Specific examples of ballast groups are illustrated below.

An alkyl group or an alkenyl group (for example, a dodecyl group, an octadecyl group, etc.), an alkoxyalkyl group (for example, a 3-(octyloxy)propyl group, a 3-(2-ethylundecyloxy)propyl group, etc., as described in Japanese Patent Publication No. 27563/64, etc.), an alkylaryl group (for example, a 4-nonylphenyl group, a 2,4-di-tert-butylphenyl group, etc.), and alkylaryloxyalkyl group (for example, a 2,4-di-tert-pentylphenoxymethyl group, an α-(2,4-di-tert-pentylphenoxy)propyl group, a 1-(3-pentadecylphenoxy)ethyl group, etc.), an acylamidoalkyl group (for example, a group described in U.S. Pat. Nos. 3,337,344 and 3,418,129, a 2-(N-butylhexadecanamido) ethyl group, etc.), an alkoxyaryl or aryloxyaryl group (for example, a 4-(n-octadecyloxy)phenyl group, a 4-(4-n-dodecylphenyloxy)phenyl group, etc.), a residue containing both an alkyl or alkenyl long-chain aliphatic group and a water-solubilizing group such as a carboxy group or a sulfo group (for example, a 1-carboxymethyl-2-nonadecenyl group, a 1-sulfoheptadecyl group, etc.), an alkyl group substituted with an ester group (for example, a 1-ethoxycarbonylheptadecyl group, a 2-(n-dodecyloxycarbonyl)ethyl group, etc.), an alkyi group substituted with an aryl group or a heterocyclic group (for example, a 2-[4-(3-methoxycarbonyluneicosanamido)phenyl]ethyl group, a 2-[4-(2-n-octadecylsuccinimido)phenyl]ethyl group, etc.), and an aryl group substituted with an aryloxyalkoxycarbonyl group (for example, a 4-[2-(2,4-di-tert-pentylphenoxy)-2-methylpropyloxycarbonyl]phenyl group, etc.).

Of the above-described organic ballast groups, those bonded to a bridging group as represented by the following general formulae are particularly preferred.

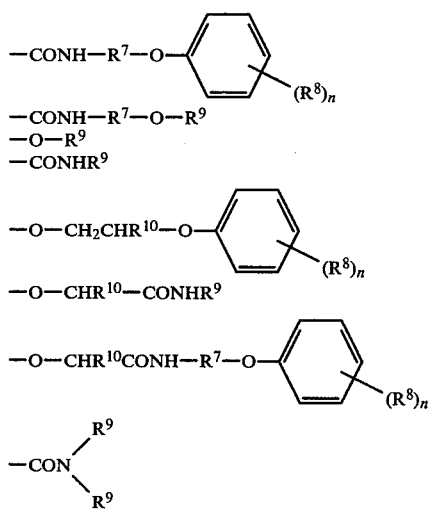

(III)
(IV)
(V)
(VI-1)
(VI-2)
(VI-3)
(VI-4)
(VI-5)

wherein $R^7$ represents an alkylene group having 1 to 10 carbon atoms, preferably 1 to 6 carbon atoms (such as a propylene group, a butylene group, etc.); $R^8$ represents a hydrogen atom or an alkyl group having 1 to 10 carbon atoms, preferably 1 to 6 carbon atoms (such as a tert-amyl group, etc.); n represents an integer of 1 to 5 (preferably 1 to 2); $R^9$ represents an alkyl group having 4 to 30 carbon atoms, preferably 10 to 20 carbon atoms (such as a dodecyl group, a tetradecyl group, an octadecyl group, etc.) and in formula (VI-5) the $R^9$'s may be different; $R^{10}$ represents an alkyl group having 1 to 8 carbon atoms with preferable examples being a methyl group and an ethyl group.

Specific examples of the sulfamoyl groups represented by the formula (II) are illustrated below:

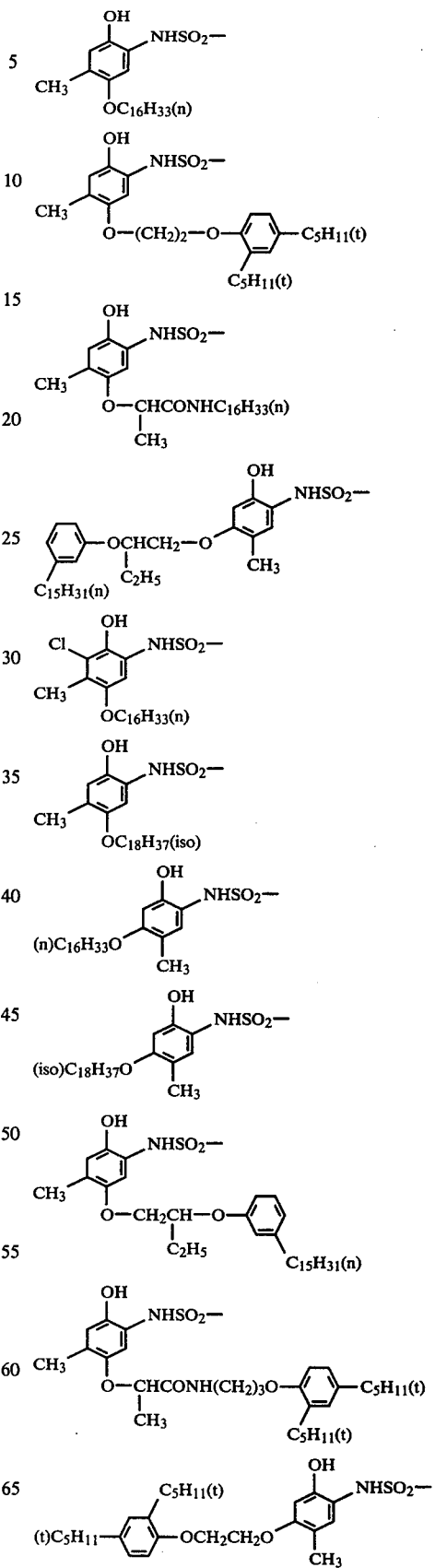

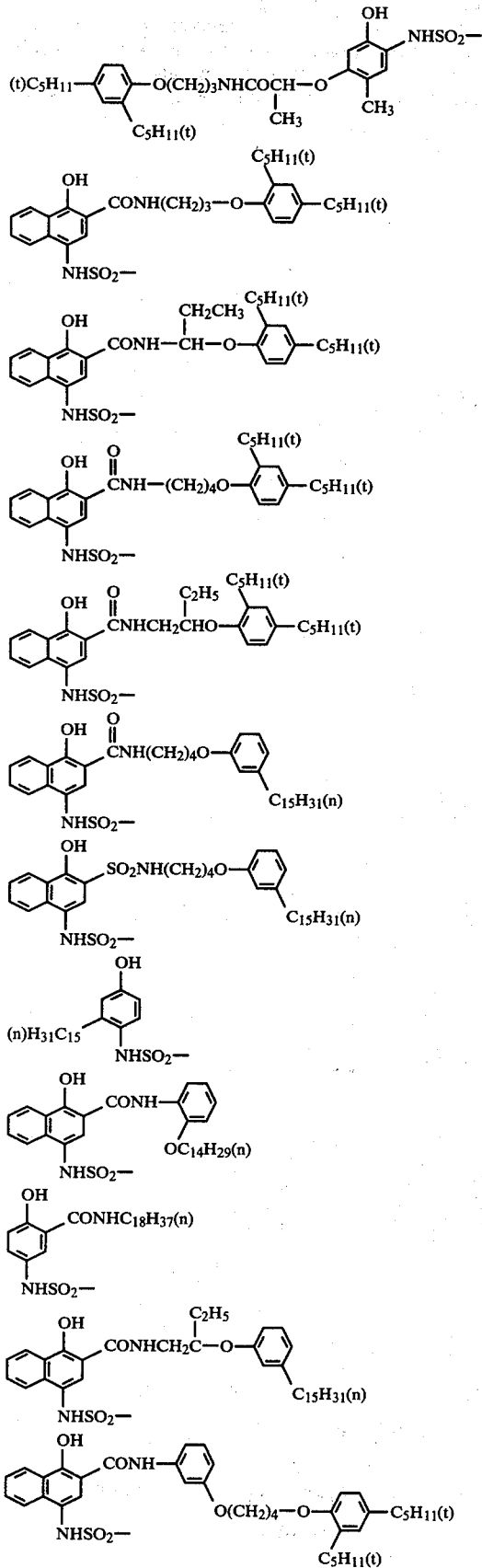

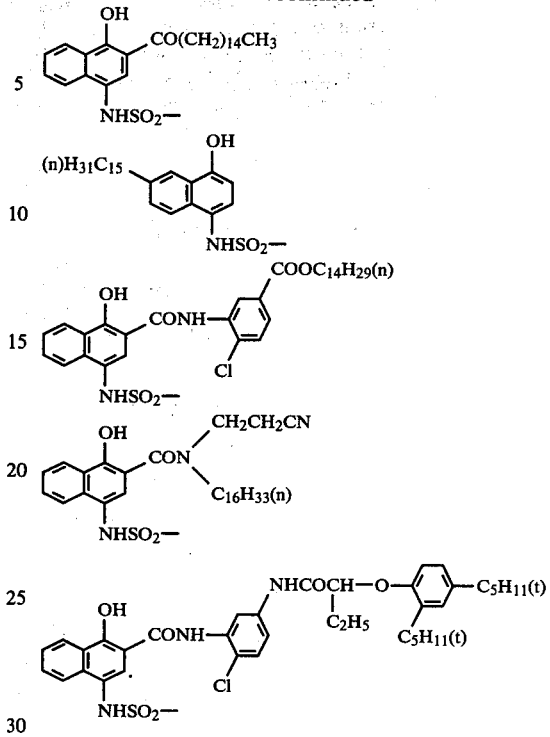

Furthermore, the groups described in *Research Disclosure*, Vol. 130, No. 13024 (February, 1975) are useful as the redox center.

A preferred compound according to the present invention is a compound represented by the above-described general formula (I), and in which $R^1$ and $R^2$ are bonded to each other to form a pyrrolidine ring or a morpholine ring wherein $R^1$ and $R^2$ represent —$(CH_2)_2$— or —$(CH_2)_2$—O—$(CH_2)_2$—, or $R^1$ represents —$CH_2CH_2OCH_3$ and $R^2$ represents an alkyl group having 1 to 3 carbon atoms or a substituted alkyl group having 1 to 3 carbon atoms (such as a methyl group, an ethyl group, an n-propyl group, an isopropyl group, a methoxyethyl group, etc.); $Q^1$ represents a sulfamoyl group represented by the formula —$SO_2NR^3R^4$, wherein $R^3$ and $R^4$, which may be the same or different, each represents a hydrogen atom, a straight chain or branched chain alkyl group having 1 to 4 carbon atoms or $R^3$ and $R^4$ can combine directly or through an oxygen atom to form a 5-membered or 6-membered ring; $Q^2$ represents a hydroxy group substituted at the 5-position or the 8-position with respect to G or an —NHSO$_2R^{4a}$ group substituted at the 5-position where $R^{4a}$ represents a straight chain or branched chain alkyl group having 1 to 4 carbon atoms; m is 0; and Y—NHSO$_2$— represents a sulfamoyl group represented by the general formula (II).

A particularly preferred compound according to the present invention is a compound represented by the above-described general formula (I), and in which the amino group —$NR^1R^2$ is positioned at the 4-position with respect to the azo group; $R^1$ and $R^2$ are bonded to each other, as —$(CH_2)_2$—O—$(CH_2)_2$— or —$(CH_2)_4$—, to form a morpholine ring or a pyrrolidine ring; $Q^1$ represents a sulfamoyl group represented by the formula —$SO_2NR^3R^4$, wherein $R^3$ represents a hydrogen atom and $R^4$ represents a tert-butyl group or an isopropyl group; $Q^2$ represents a hydroxy group or a —NHSO$_2$R$^{4a}$ group where R$^{4a}$ represents an alkyl group having 1 to 4 carbon atoms at the 5-position with respect to G, more preferably $Q^2$ represents an —NHSO$_2$CH$_3$ group; m=0, and Y—NHSO$_2$— represents an o-hydroxyphenylsulfamoyl group having an alkyl group at the meta position to the hydroxy group in addition to a ballast group.

Specific examples of dye releasing redox compound according to the present invention are illustrated below. However, the present invention should not be construed as being limited to these specific examples.

Compound 1

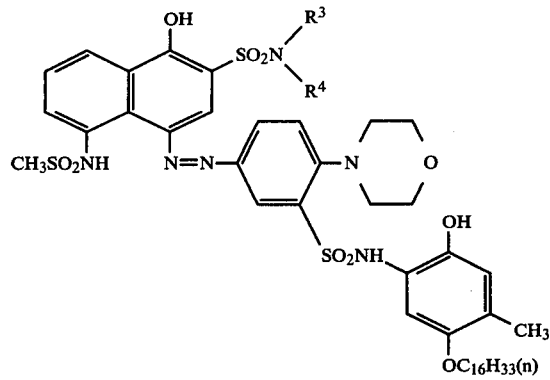

wherein R$^3$ is H and R$^4$ is —C(CH$_3$)$_3$

Compound 2

Same compound as Compound 1 except for R$^3$ is H and R$^4$ is —C$_4$H$_9$-n

Compound 3

Same compound as Compound 1 except for R$^3$ and R$^4$ are —C$_2$H$_5$

Compound 4

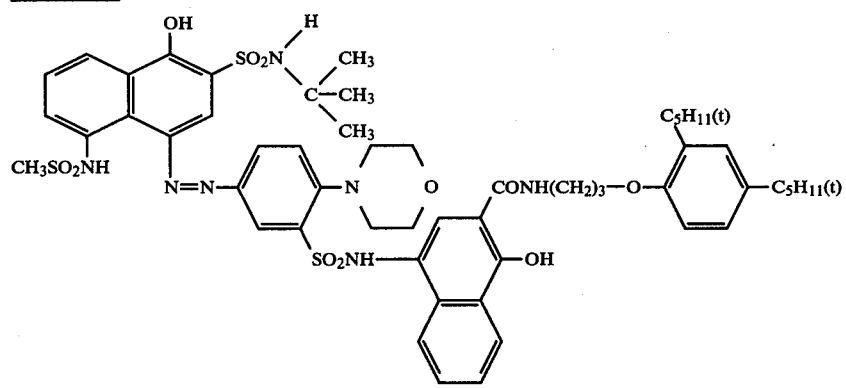

Compound 5

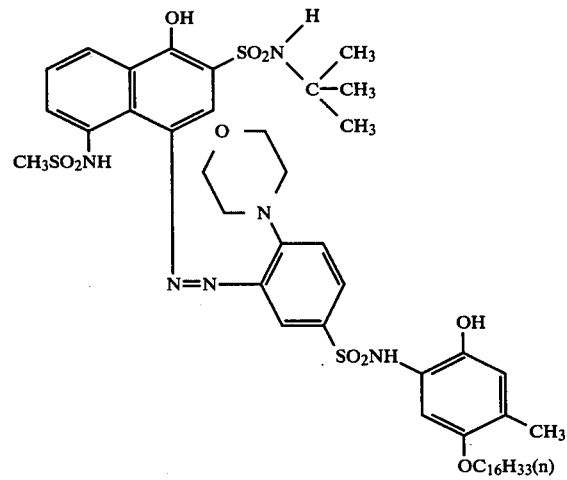

Compound 6

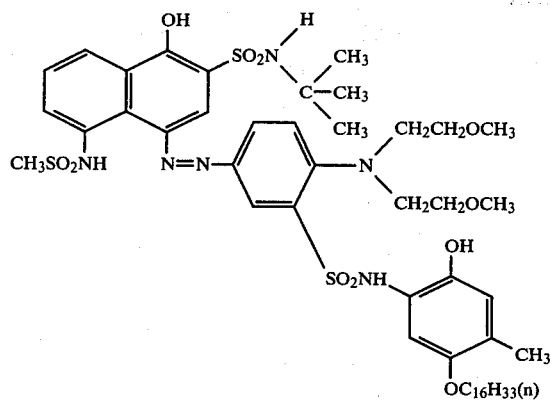
Compound 7
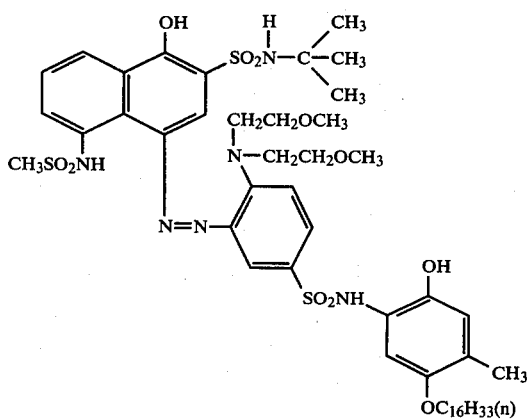
Compound 8
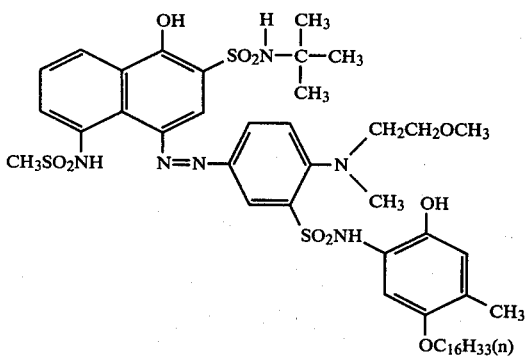
Compound 9
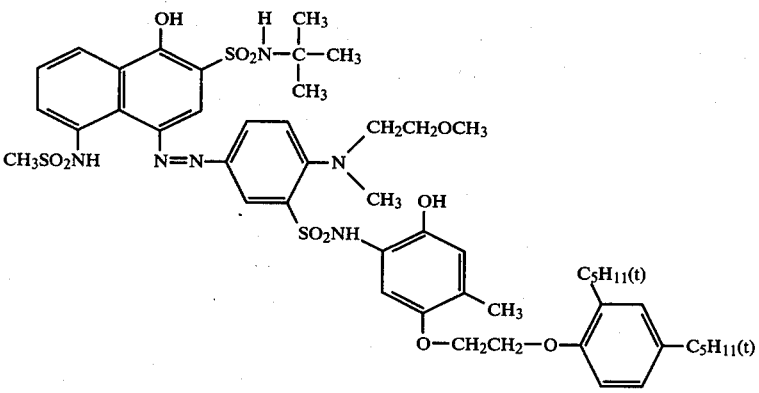
Compound 10

-continued
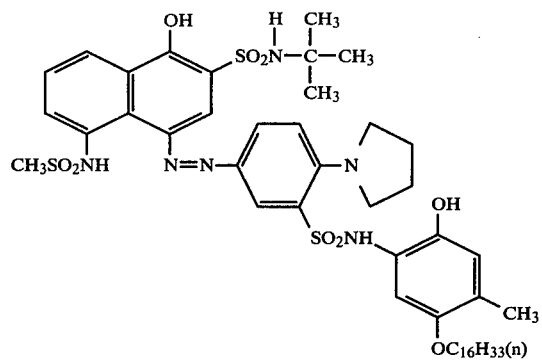
Compound 11
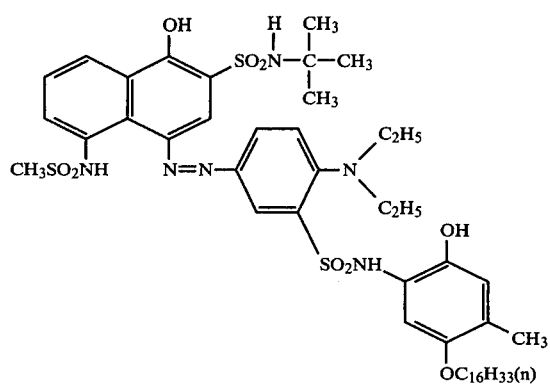
Compound 12
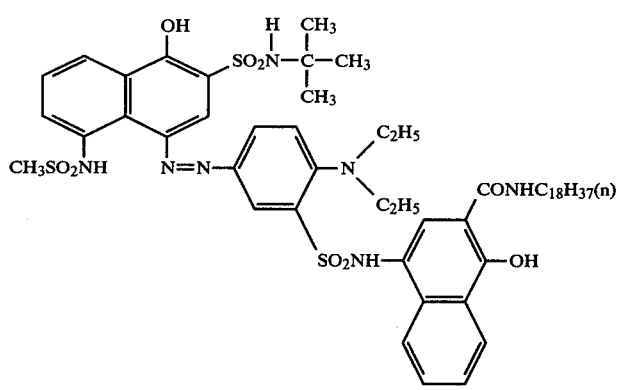
Compound 13
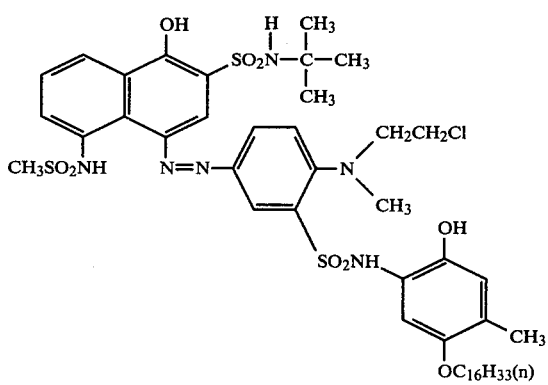
Compound 14

-continued
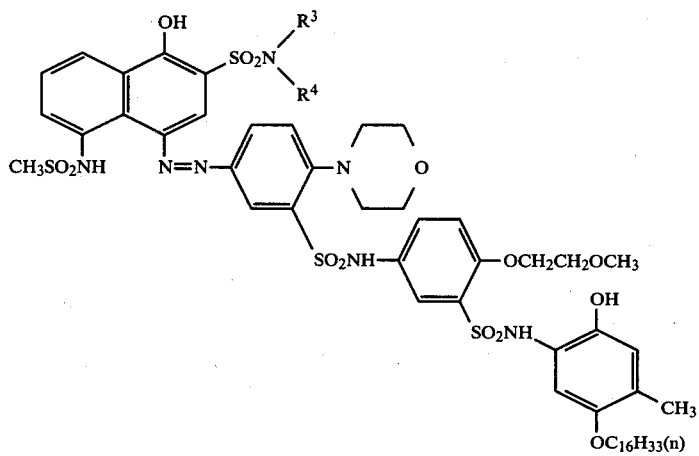
wherein $R^3$ is H and $R^4$ is $-\underset{\underset{CH_3}{|}}{\overset{\overset{CH_3}{|}}{C}}-CH_3$
Compound 15
Same compound as Compound 14 except for $R^3$ is H and $R^4$ is $-C_4H_9$-n
Compound 16
Same compound as Compound 14 except for $R^3$ and $R^4$ are $-C_2H_5$
Compound 17
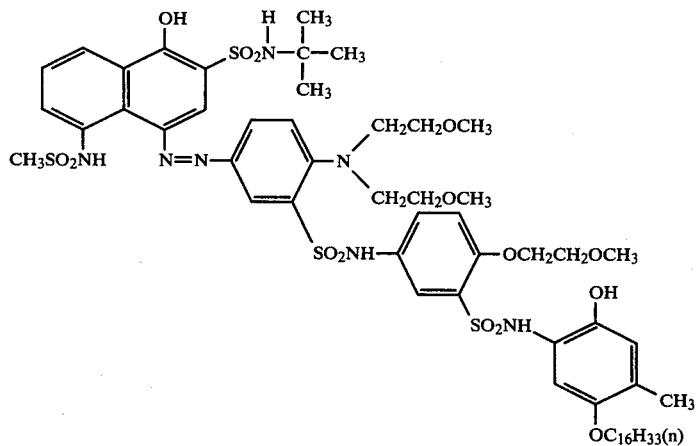
Compound 18
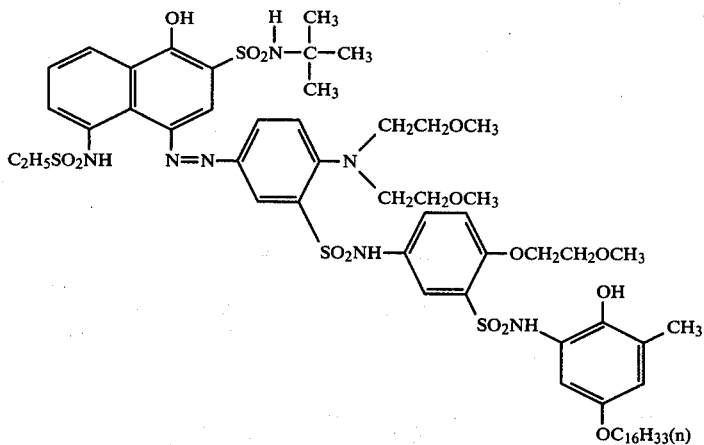
Compound 19

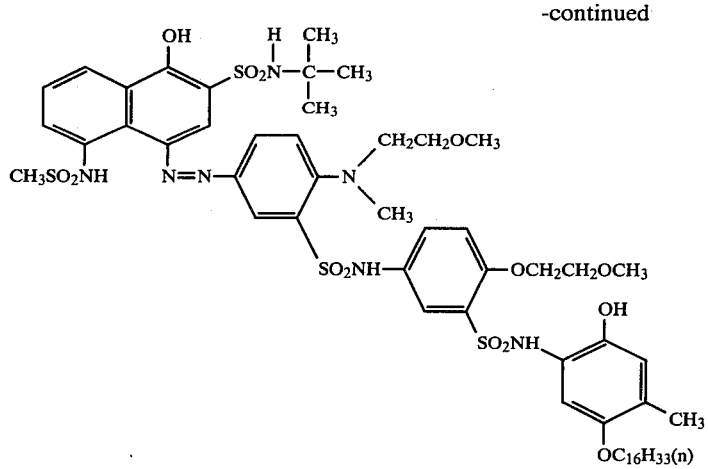

The compound according to the present invention releases a novel magenta dye compound represented by the following general formulae (VII) or (VIII):

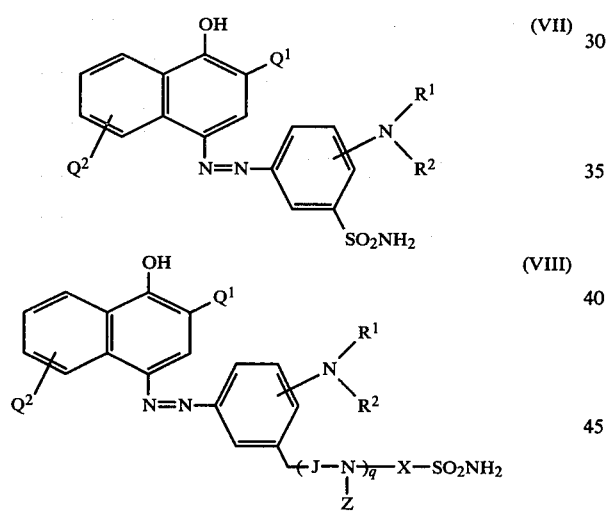

wherein $Q^1$, $Q^2$, $R^1$, $R^2$, J, Z, X and q each has the same meaning as defined in the general formula (I), when the compound is oxidized under alkaline conditions.

The compound according to the present invention can be obtained by a coupling reaction of a compound represented by the formula (IX) (the coupler or coupling component) with a diazo compound derived from an amine represented by the formulae (X) or (XI); or by a condensation reaction of a sulfonyl halide represented by the formula (XII) with an amine represented by the formulae (XIII) or (XIV):

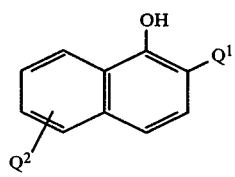

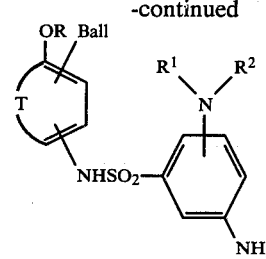

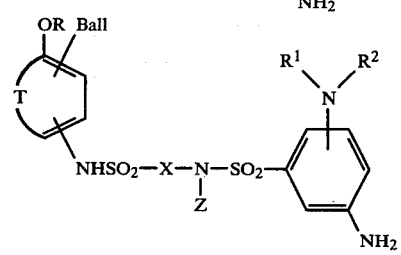

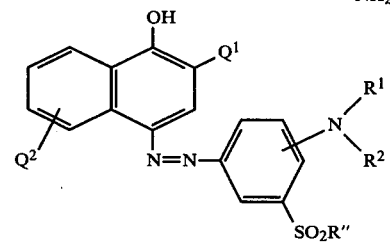

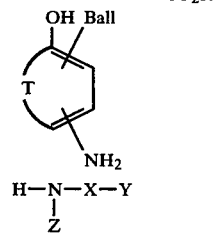

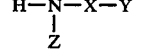

wherein $Q^1$, $Q^2$, $R^1$, $R^2$, X, Y, and Z each has the same meaning as defined in the formula (I); T and Ball each has the same meaning as defined in the formula (II): R represents a hydrogen atom or an acetyl group; and R" represents a halogen atom (for example, a chlorine atom, a fluorine atom, etc.).

When the compound according to the present invention is obtained by a coupling reaction of a compound represented by the formula (IX) with a diazo compound derived from an amine represented by the formula (X) wherein R is H or the formula (XI) wherein R is H, it is desirable to conduct the diazotization and the coupling reaction at a temperature as low as possible (e.g., about −20° C.) in order to prevent oxidation of the redox center. More preferably, a compound in which the —OH group in the redox center is protected such as a compound of the formula (XI) wherein R is acetyl is employed. In this case, the diazotization and the subsequent coupling reaction can be carried out at about 0° C., since oxidation of the redox center is suppressed by the protective group. The acetyl group, as a protective group, is easily split with an acid or an alkali after the coupling reaction to form the compound according to the present invention.

The amine represented by the formulae (X) or (XI) is obtained by a condensation reaction of a sulfonic acid halide represented by the formula (XV) with an amine represented by the formulae (XIII) or (XIV) and reduction of the nitro group or acetylation and reduction of the nitro group in the following manner.

alkali metal or an alkaline earth metal (for example, sodium hydroxide, potassium hydroxide, barium hydroxide, calcium hydroxide, etc.), an aliphatic amine (for example, triethylamine, etc.), an aromatic amine (for example, N,N-diethylaniline, etc.), a heteroaromatic amine (for example, pyridine, quinoline, α-, β- or γ-picoline, lutidine, collidine, 4-(N,N-dimethylamino)-pyridine, etc.), or a heterocyclic base (for example, 1,5-diazabicyclo [4,3,0]nonene-5, 1,8-diazabicyclo[5,4,-0]undecene-7, etc.). A heteroaromatic amine (preferably pyridine) is particularly preferred of the above-described basic compounds where a compound represented by the formula (XV) wherein R" is a chlorine atom, that is, a sulfonyl chloride, is used.

The acetylation of the —OH group in the redox moiety of the compound represented by the formula (XVI) or (XVII) can be easily conducted under conventional conditions, for example, by heating with acetic anhydride in the presence of a metal salt (for example, a sodium salt or a potassium salt) of acetic acid.

Typical examples of reduction reaction of the com-

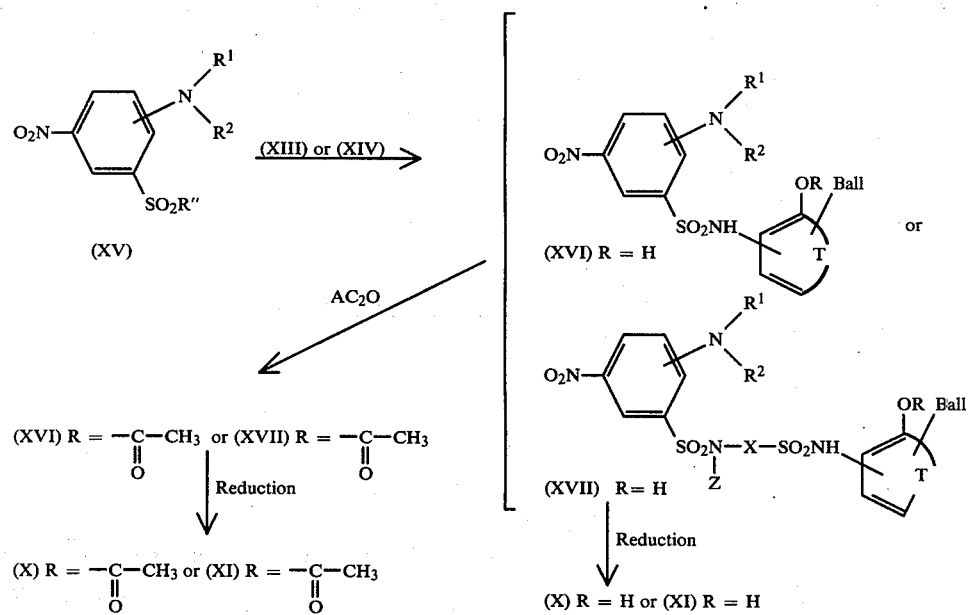

wherein $R^1$, $R^2$, X and Z each has the same meaning as defined in the formula (I), T and Ball each has the same meaning as defined in the formula (II), R represents a hydrogen atom or an acetyl group and R" represents a halogen atom (for example, a chlorine atom, a fluorine atom, etc.).

Usually, the condensation reaction of a compound represented by the formula (XV) with a compound represented by the formula (XIII) or (XIV) is preferably carried out in the presence of 1 to 2 equivalents of a basic compound (acid removing agent). Examples of suitable basic compounds include a hydroxide of an pound represented by the formula (XVI) or (XVII) to obtain a compound represented by the formula (X) or (XI) are a catalytic hydrogenation (using Raney nickel, palladium-carbon or active carbon as a catalyst), a reduction with iron powder, a hydrazine reduction, etc.

The compound represented by the formula (XV) can be synthesized by obtaining the compound represented by the formula (XIX) directly or through a compound represented by the formula (XX) from a compound represented by the formula (XVIII) and then converting the sulfonic acid group to a sulfonyl halide using a halogenating agent in the following manner:

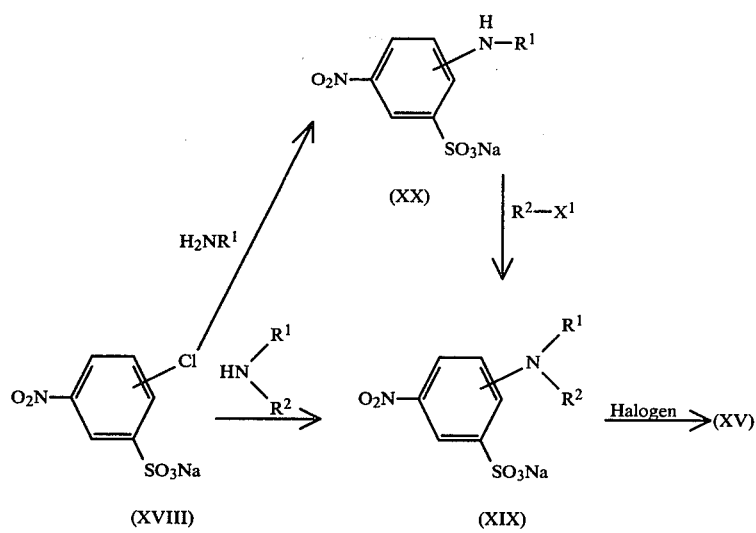

wherein $R^1$ and $R^2$ each has the same meaning as defined in the formula (I) and $X^1$ represents a halogen atom (for example, a chlorine atom or a bromine atom).

The compound represented by the formula (XIX) can be synthesized by heating the compound represented by the formula (XVIII) with an excess amount of a compound of an amine of the formula $HNR^1R^2$ or by reacting the compound represented by the formula (XVIII) with a compound of the formula $H_2N—R^1$ to obtain the compound represented by the formula (XX) and then reacting the latter compound with a substituted or unsubstituted alkyl halide in the presence of an acid removing agent as described hereinbefore. In order to convert the compound of the formula (XIX) to the compound of the formula (XV), a chlorinating agent such as phosphorus oxychloride ($POCl_3$), thionyl chloride ($SOCl_2$) or phosphorus pentachloride ($PCl_5$) is preferably used. The chlorination reaction is preferably carried out in the presence of an N,N-di-substituted carbonamide such as N,N-dimethylacetamide, N-methylpyrrolidone, etc., as a catalyst.

Typical examples of the amine represented by the formula (XIII) are described, for example, in Japanese Patent Application (OPI) Nos. 113624/76, 115528/75 and 114424/74, U.S. Pat. Nos. 3,932,380 and 3,931,144 and Research Disclosure, Vol, 130, No. 13024.

Two typical methods for the preparation of the amine represented by the formula (XIV) are schematically illustrated below:

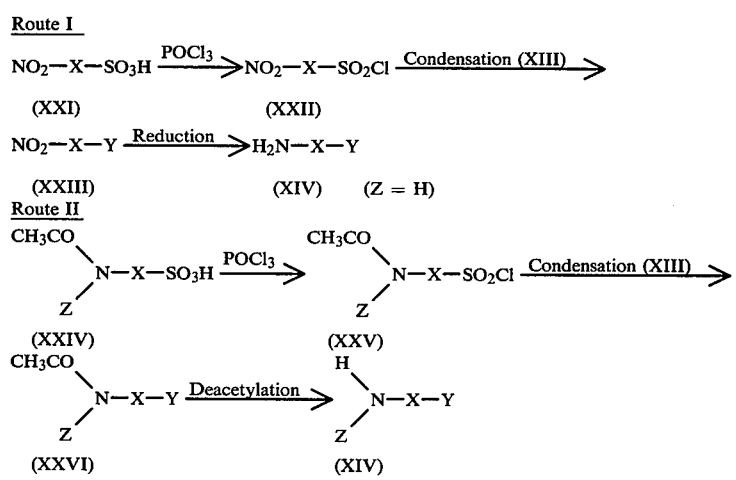

wherein X, Y and Z each has the same meaning as defined in the formula (I).

In order to obtain a compound represented by the formulae (XXIII) or (XXVI) by a condensation reaction of a sulfonyl chloride represented by the formulae (XII) or (XXV) with an o- or p-hydroxyarylamine represented by the formula (XIII), the condensation reaction is preferably carried out in the presence of a basic compound, with suitable examples of basic compounds being as described with respect to the reaction of the compound of the formula (XV) with the compound of the formulae (XIII) or (XIV).

Typical examples of reduction reactions for obtaining a compound represented by the formula (XIV) from a compound represented by the formula (XXIII) are those described for obtaining a compound represented by the formulae (X) or (XI) from a compound represented by the formulae (XVI) or (XVII). Typical examples of reactions for obtaining a compound represented by the formula (XIV) from a compound represented by the formula (XXVI) include heating the former compound with hydrochloric acid or an alkaline aqueous solution.

On the other hand, when the compound according to the present invention is synthesized by a condensation reaction of a compound represented by the formula (XII) with a compound represented by the formula (XIII) or (XIV), also the condensation reaction is preferably carried out in the presence of a basic compound, with suitable examples of basic compounds being as described with respect to the reaction of the compound of the formula (XV) with the compound of the formulae (XIII) or (XIV).

When the compound represented by the formula (XII) is synthesized from a compound represented by the formula (XXVII) described below, the methods as described for converting a compound represented by the formula (XIX) to a compound represented by the formula (XV) are also preferred.

The compound represented by the formula (XXVII) is synthesized by a coupling reaction of a diazo compound derived from an amine represented by the formula (XXVIII) described below with a compound represented by the formula (IX). Typical examples of reduction reaction for obtaining a compound represented by the formula (XXVIII) from a compound represented by the formula (XIX) are the reduction methods described for obtaining a compound represented by the formulae (X) or (XI) from a compound represented by the formulae (XVI) or (XVII). Of these methods, a catalytic hydrogenation is preferred.

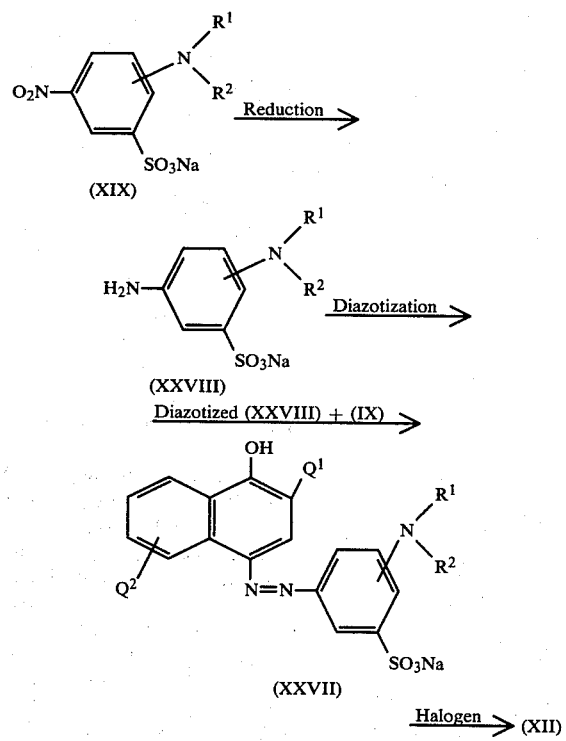

wherein $Q^1$, $Q^2$, $R^1$ and $R^2$ each has the same meaning as defined in the formula (I).

While the preparation of the dye releasing redox compound having the group represented by the general formula (II) as a redox central has been described hereinbefore, compounds having other redox center can be synthesized by analogy to the above-described synthesis methods.

Typical synthesis examples of the dye releasing redox compounds used in the present invention and intermediates thereof are illustrated in detail below.

SYNTHESIS OF INTERMEDIATES

Synthesis Example 1

Synthesis of Sodium 2-Morpholino-5-nitrobenzenesulfonate

To 80 ml of morpholine, 82.5 g (0.3 mol) of sodium 2-chloro-5-nitrobenzenesulfonate was added with stirring. The reaction mixture was heated at about 110° C. on an oil bath with stirring for 30 minutes. After cooling, 100 ml of a saturated aqueous sodium chloride solution was added to the mixture. The crystals thus-precipitated were collected by filtration and washed with acetone to obtain 88 g (yield: 90%) of sodium 2-morpholino-5-nitrobenzenesulfonate. Melting Point: 208°–210° C.

Synthesis Example 2

Synthesis of Sodium 2-[Bis(2-methoxyethyl)amino]-5-nitrobenzenesulfonate

To 30 ml of 2-methoxyethylamine, 27.5 g (0.1 mol) of sodium 2-chloro-5-nitrobenzenesulfonate was added. The reaction mixture was heated on a steam bath with stirring for 1 hour. After cooling, 100 ml of a saturated aqueous sodium chloride solution was added to the mixture. The crystals thus-precipitated were collected by filtration and washed with acetone to obtain about 30 g (yield: 87%) of sodium 2-(2-methoxyethylamino)-5-nitrobenzenesulfonate. This compound (30 g) was suspended in 100 ml of dimethylformamide. To the mixture anhydrous potassium carbonate (20 g) and methoxyethyl bromide (21g) were added, and heated on a steam bath with stirring for 1 hour. The reaction mixture was added to 100 ml of water and the insoluble materials were removed by filtration. To the filtrate an aqueous hydrochloric acid was added to render an acid condition. The crystals thus-precipitated were collected by filtration to obtain about 21 g (yield: 60%) of sodium 2-bis(2-methoxyethyl)amino-5-nitrobenzensulfonate. Melting Point: 202°–204° C.

SYNTHESIS OF DYE RELEASING REDOX COMPOUND

Synthesis 1: Synthesis of Compound 1

(a) Synthesis of 2-Morpholino-5-nitrobenzenesulfonylchloride 31 g (0.1 mol) sodium 2-morpholino-5-nitrobenzenesulfonate obtained in Synthesis Example 1 of intermediates described above and 60 ml of (0.67 mol) of phosphorus oxychloride were added to 300 ml of acetonitrile and the mixture was refluxed by heating for 2 hours. After cooling, the reaction mixture was added to 600 ml of ice water. The crystals thus-precipitated were collected by filtration. Yield: 18.5 g (60%). Melting Point: 118°–120° C. (b) Synthesis of 2-(2'-Morpholino-5'-nitrobenzenesulfonamido)-4-hexadecyloxy-5-methylphenol To a solution of N,N-dimethylamide (60 ml) containing 15.3 g (0.05 mol) of the compound obtained in Step (a) above and 20 g (0.05 mol) 2-amino-5-hexadecyloxy-5-methylphenol hydrochloride, 12 ml (0.15 mol) of pyridine was added dropwise at below 10° C. After completion of the addition, the mixture was stirred at room temperature for 1 hour. To the reaction mixture, methanol (200 ml) was added and heated on a water bath. After cooling, the crystals thus-precipitated were collected by filtration. Yield: 31 g (98%). Melting Point: 9.25°–94° C.

(c) Synthesis of 2-(2'-Morpholino-5'-nitrobenzenesulfonamido)-4-hexadecyloxy-5-methylphenyl acetate A mixture of 19.5 g (0.03 mol) of the compound obtained in Step (a) above, acetic anhydride (10 ml), acetic acid (150ml) and sodium acetate (5 g) was heated at about 120° C. on an oil bath with stirring for 1 hour. After cooling, the reaction mixture was added to ice water (500 ml) and the crystals thus-precipitated were collected by filtration and washed with methanol. Yield: 20 g (96%). Melting Point: 95°–96° C.

(d) Synthesis of 2-(2'-Morpholino-5'-aminobenzenesulfonamido)-4-hexadecyloxy-5-methylphenol acetate 19.5 g (0.029 mol) of the compound obtained in Step (c) above, reduced iron (5.3 g), triirontetraoxide (2.7 g) and ammonium chloride (0.4 g) were suspended in isopropanol (300 ml). To the mixture, a mixed solution of water (40 ml) and acetic acid (2 ml) was added dropwise while refluxing with heating. After the completion of the addition, the mixture was refluxed wih heating for 2 hours and the insoluble materials were removed by filtration while hot. The filtrate was added to water (300 ml) and the crystals thus-precipitated were collected by filtration. Yield: 16.4 g (86%). Melting Point: 110°–112° C.

(e) Synthesis of Acetyl Derivative of Compound 1

10 g (0.0155 mol) of the compound obtained in Step (d) above was added to a mixed solution of methyl Cellosolve (80 ml) and concentrated hydrochloric acid (6.3 ml) and the mixture was stirred at about 0° C. To the reaction solution, a mixed solution of water (3 ml) containing sodium nitrite (1.25 g) and methyl Cellosolve (15 ml) was added dropwise while maintaining the temperature of the reaction mixture at 0° to 5° C. and further stirred for 1 hour.

The reaction solution of diazonium salt thus-prepared was added to a solution of methyl Cellosolve (55 ml) containing 2-tert-butyl sulfamoyl-5-methanesulfonamide-1-naphthol (5.5 g, 0.0155 mol) sodium acetate 83.9 g) at about 0° C. and stirred for 1 hour. 10 ml of concentrated hydrochloric acid was added to the reaction mixture to render an acid condition and te mixture was added to water. The crystals thus-precipitated were collected by filtration and recrystallized from acetonitrile. Yield: 8.5 g (55%).

(f) Synthesis of compound 1

8.9 g of the acetyl derivative obtained in Step (e) above was completely dissolved in a solvent mixture of methanol (100 ml) and acetonitrile (50 ml) and to the solution concentrated hydrochloric acid (20 ml) was added. The mixture was refluxed with heating for 2 hours. After cooling to room temperature, thecrystals thus-precipitated were collected by filtration, washed with methanol with heating to obtain Compound 1. Yield: 7.2 g (84%). Melting Point: 101°–104° C. $\lambda DMF/max = 562$ nm ($\epsilon = 4.77 \times 10^4$).

Turning now to the reproduction of natrual color by subtractive color photography, a light-sensitive element comprising at least two combinations of each of a silver halide emulsion having a selective spectral sensitivity in a certain wavelength region and a compound capable of providing a dye having a selective spectral absorption at the same wavelength region as the emulsion is used. In particular, a light-sensitive element comprising a combination of a blue-sensitive silver halide emulsion and a compound capable of providing a yellow dye, a combination of a green-sensitive silver halide emulsion and a compound capable of providing a magenta dye, and a combination of a red-sensitive silver halide emulstion and a compound capable of providing a cyan dye is useful. As a matter of course, diffusible dye-releasing redox compounds of the present invention can be used as the above-described compounds capable of providing the dye. These combinations of units of the silver halide emulsions and the dye providing compounds may be coated on a support as layers in a face-to-face relationship or may be coated on a support as a layer containing a mixture of particles of the silver halides and the dye providing compounds in a binder.

In a preferred multilayer structure, a blue-sensitive silver halide emulsion layer, a green-sensitive silver halide emulsion layer and a red-sensitive silver halide emulsion layer are positioned in this order from the side of incident light of exposure and, in particular, it is desirable for a yellow filter layer to be positioned between the blue-sensitive silver halide emulsion layer and the green-sensitive silver halide emulsion layer when a highly sensitive silver halide emulsion containing silver iodide is used. The yellow filter layer usually contains a dispersion of yellow colloidal silver, a dispersion of an oil-soluble yellow dye, an acid dye mordanted to a basic polymer, or a basic dye mordanted to an acid polymer.

It is advantageous for the silver halide emulsion layers to be separated from each other by an interlayer. The interlayer acts to prevent the occurrence of undesirable interactions between the differently color-sensitized silver halide emulsion layers. The interlayer employed in such a case is usually composed of a hydrophilic polymer such as gelatin, polyacrylamide, a partially hydrolyzed product of polyvinyl acetate, etc., a polymer containing fine pores formed from a latex of a hydrophilic polymer and a hydrophobic polymer, e.g., as described in U.S. Pat. No. 3,625,685, or a polymer whose hydrophilic property is gradually increased by the processing composition such as calcium alginate, as described in U.S. Pat. No. 3,384,483, individually or as a combination thereof.

The silver halide emulsions which can be used in the present invention are a dispersion of silver chloride, silver bromide, silver chlorobromide, silver iodobromide, silver chloroiodobromide or a mixture thereof in a hydrophilic colloid. The halide composition of the silver halide is selected depending on the purpose of using the photographic materials, but a silver bromide emulsion, a silver iodobromide emulsion or a silver chloroiodobromide emulsion having a halide composition of 0 to 10 mol % iodide, less than 30 mol % chloride, and the rest bromide is particularly preferred.

Also, silver halide emulsions which form a latent image on the surface of the silver halide grains, silver halide emulsions which form a latent image inside the silver halide grains as described in U.S. Pat. Nos. 2,592,550, 3,206,313, etc., and direct positive silver halide emulsions can be used in the present invention.

The silver halide emulsions used in the present invention can possess, if desired, a color sensitivity expanded with a spectral sensitizing dye or dyes. Examples of useful spectral sensitizers are cyanine, merocyanine, holopolar cyanine, styryl, hemicyanine, oxanole, hemioxanole, etc., dyes.

The dye releasing redox compound used in the present invention can be dispersed in a hydrophilic colloid as a binder using various known methods.

A suitable amount of dye releasing redox compound which can be used in the present invention is about $2.5 \times 10^{-3}$ to about $2.5 \times 10^{-5}$ mol/m$^2$, preferably $1 \times 10^{-3}$ to $1 \times 10^{-5}$ mol/m$^2$.

The light-sensitive sheet of the present invention is prepared by coating directly or indirectly at least one light-sensitive silver halide photographic emulsion layer with the dye releasing redox compound according to the present invention associated therewith onto a substantially planar material which does not undergo large dimensional changes during processing. Examples of suitable supports which can be used are cellulose acetate films, polystyrene films, polyethylene terephthalate films, polycarbonate films, etc., as are used as supports for conventional photographic materials. Other examples of suitable supports are papers and papers coated with a water-impermeable polymer such as polyethylene.

Examples of methods of forming diffusion transfer color photographic images by using dye releasing redox compounds are described in Japanese Patent Application (OPI) Nos. 114424/74 and 33826/73, Belgian Pat. No. 788,268, etc. These methods can be used with the dye releasing redox compound according to the present invention.

One embodiment of a series of steps for obtaining color diffusion transfer images using a dye-releasing redox compound according to the present invention is described below.

(A) A light-sensitive element comprising a support having thereon at least one light-sensitive silver halide emulsion layer with the dye-releasing redox compound according to the present invention associated therewith is imagewise exposed.

(B) An alkaline processing composition is spread on the above-described light-sensitive silver halide emulsion layer whereby development of all light-sensitive silver halide emulsion layers in the presence of a developing agent for silver halide is conducted.

(C) As a result, an oxidation product of the developing agent produced in proportion to the amount of exposure cross-oxidizes the dye-releasing redox compound.

(D) The above-described oxidation product of the dye-releasing redox compounds splits to release a diffusible dye.

(E) The released diffusible dye imagewise diffuses to form a transferred image on an image-receiving layer (directly or indirectly) adjacent the light-sensitive silver halide emulsion layer.

In the above-described process, any silver halide developing agents which can cross-oxidize the dye-releasing redox compound can be used. These developing agents may be incorporated into the alkaline processing composition or may be incorporated into appropriate photographic layers of the light-sensitive element. Specific examples of suitable developing agents which can be used in this invention are, for example, hydroquinones; aminophenols such as N-methylaminophenol; pyrazolidones such as phenidone (1-phenyl-3-pyrazolidone), dimedone (1-phenyl-4,4-dimethyl-3-pyrazolidone), 1-phenyl-4-methyl-4-oxymethyl-3-pyrazolidone; phenylenediamines such as N,N-diethyl-p-phenylenediamine, 3-methyl-N,N-diethyl-p-phenylenediamine, 3-methoxy-N-ethoxy-p-phenylenediamine, etc.

Of the above-indicated developing agents, black-and-white developing agents having the capability, in general, of reducing the occurrence of stains in image-receiving layers are particularly preferred in comparison with color developing agents such as phenylenediamines.

When the dye-releasing redox compound according to this invention is used, the transferred image formed in the image-receiving layer is a negative image and the image where a conventional surface latent image forming type emulsion is used without using a reversal mechanism. On the other hand, where a direct positive silver halide emulsion (including an emulsion which can provide a direct reversal positive image by fogging during development after exposure, for example, an internal latent image forming type silver halide emulsion or a solarization type silver halide emulsion) is employed as the silver halide emulsion in the above-described case, the transferred image formed in the image-receiving layer is a positive image.

Solarization type silver halide emulsions as described in C. E. K. Mees, *The Theory of the Photographic Process*, pp. 261–297, Macmillan Co., New York (1942) can be used in this invention. These solarization type silver halide emulsions may be prepared using methods described in, for example, British Pat. Nos. 443,245 and 462,730 and U.S. Pat. Nos. 2,005,837, 2,541,472, 3,367,778, 3,501,305, 3,501,306 and 3,501,307.

Also, internal latent image forming type silver halide emulsions as described in, for example, U.S. Pat. Nos. 2,592,250, 3,761,276 and 3,923,513, etc., can be advantageously used in this invention. Typical examples of fogging agents which can be used for preparing this type of silver halide emulsion are the hydrazines described in U.S. Pat. Nos. 2,588,982 and 2,563,785, the hydrazide and hydrazone described in U.S. Pat. No. 3,227,552, and the quaternary salt compounds described in British Pat. No. 1,283,835, Japanese Patent Publication No. 38164/74, and U.S. Pat. Nos. 3,734,738, 3,719,494 and 3,615,615.

Furthermore, the diffusion inhibitor releasing (DIR) reversal silver halide emulsion system as described in U.S. Pat. Nos. 3,227,551, 3,227,554 and 3,364,022 or the reversal silver halide system using dissolution physical development as described in British Pat. No. 904,364 can be employed in the case of using the dye-releasing redox compound of this invention.

The dye-releasing redox compound according to the present invention is useful when it is used alone, but can be used together with other compounds depending on the effect desired. For instance, of the compounds according to the present invention the compounds which release dyes having an absorption in a longer wavelength region ($\lambda$ max: about 550 to 570 nm) such as Compounds 5 and 7 described above are preferably used together with a dye releasing-redox compound which releases a dye having an absorption in a shorter wavelength region ($\lambda$ max: about 520 to 550 nm) in a molar proportion of the former to the latter being about 10:90 to about 50:50. Examples of dye releasing-redox compounds which release a dye having an absorption in a shorter wavelength region which can be used include, for example, Compounds 6, 8, 9, 11, 12, 13 and 17 to 19 and the compounds described below. These compounds can be synthesized in the manner disclosed in U.S. patent application Ser. No. 911,571, filed June 1, 1978.

Compound A-1

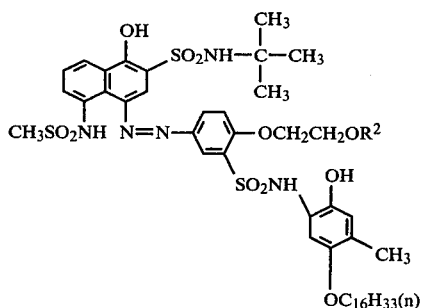

wherein $R^2$ is $CH_3$

Compound A-2

Same compound as Compound A-1 except $R^2$ is $C_2H_5$.

Compound A-3

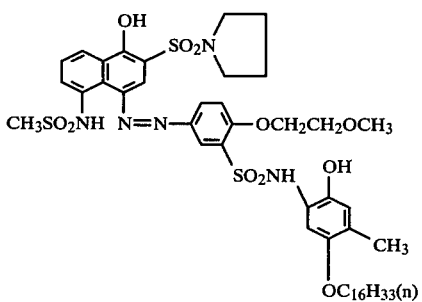

wherein $R^3$ is H

Compound A-4

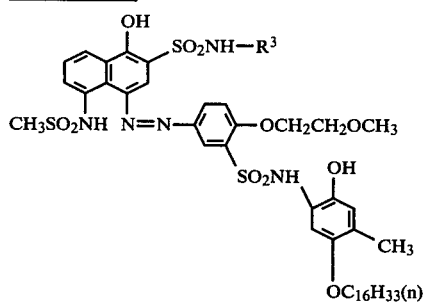

Compound A-5

Same compound as Compound A-4 except $R^3$ is $CH_3$

Compound A-6

Same compound as Compound A-4 except $R^3$ is n-$C_4H_9$

Compound A-7

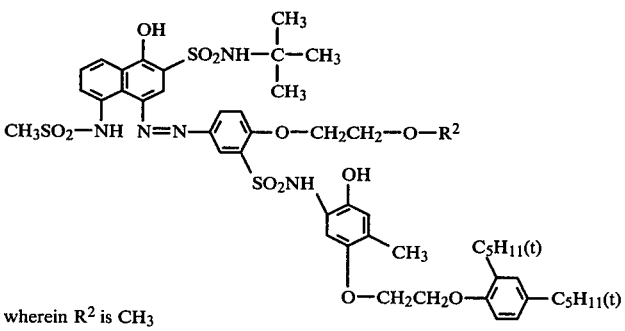

wherein $R^2$ is $CH_3$

Compound A-8

Same compound as Compound A-7 except $R^2$ is $C_2H_5$

Compound A-9

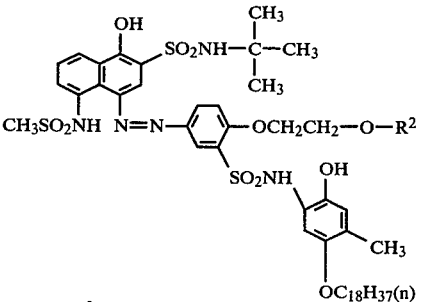

wherein $R^2$ is $CH_3$

Compound A-10

Same compound as Compound A-9 except $R^2$ is $C_2H_5$

Compound A-11

-continued
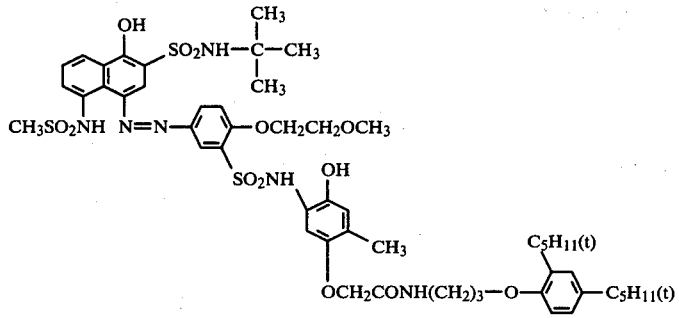
Compound A-12
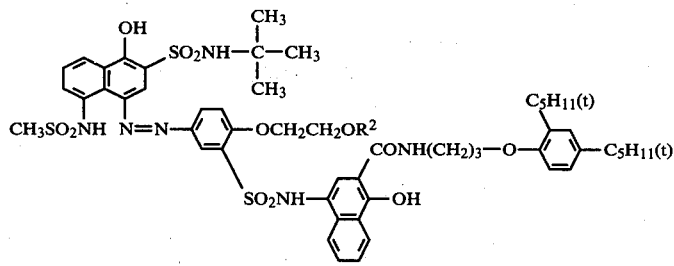
Compound A-13
Same compound as Compound A-12 except $R^2$ is $C_2H_5$
wherein $R^2$ is $CH_3$
Compound A-14
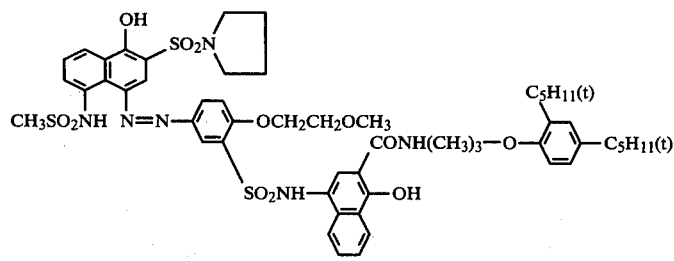
Compound A-15
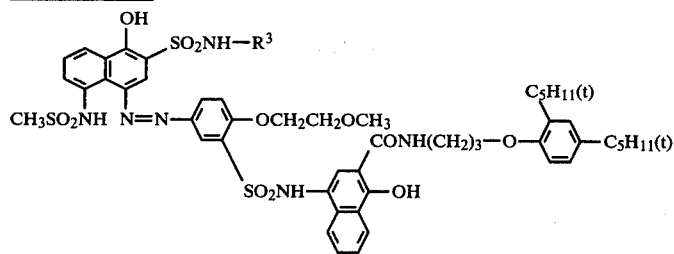
Compound A-16
Same compound as Compound A-15 except $R^3$ is $CH_3$
wherein $R^3$ is H
Compound A-17
Same compound as Compound A-15 except $R^3$ is n-$C_4H_9$
Compound A-18
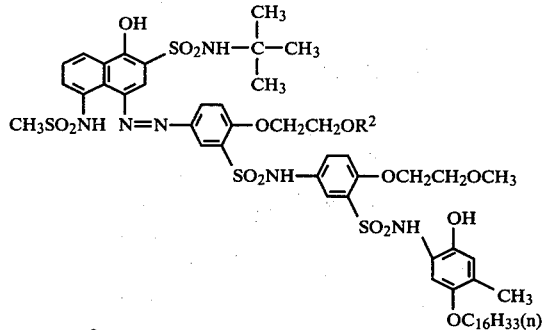
Compound A-19
Same compound as Compound A-18 except $R^2$ is $C_2H_5$
wherein $R^2$ is $CH_3$
Compound A-20

-continued

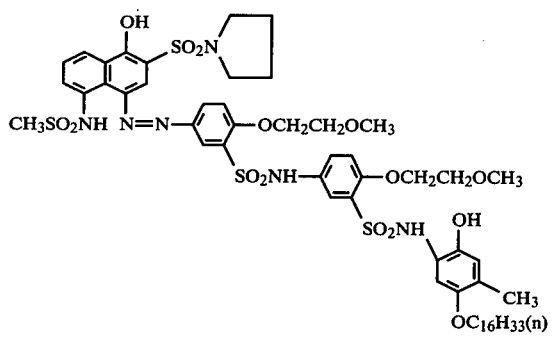

Compound A-21

Compound A-22

Same compound as Compound A-21 except $R^3$ is $CH_3$

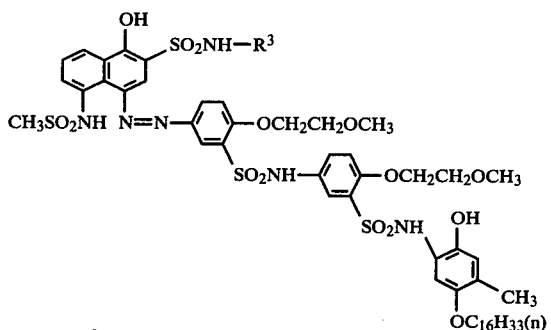

wherein $R^3$ is H

Compound A-23

Same compound as Compound A-21 except $R^3$ is n-$C_4H_9$

Compound A-24

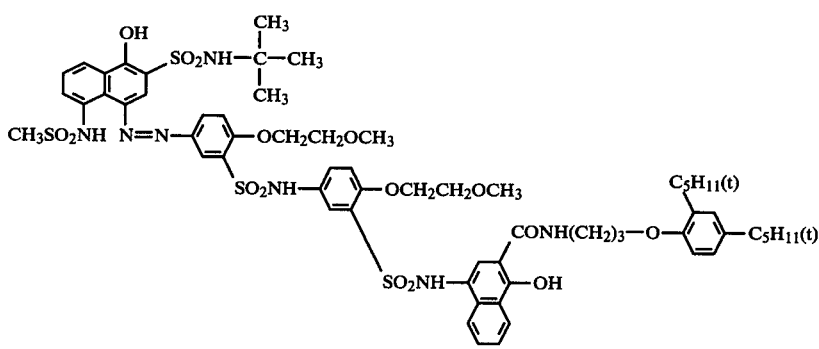

Compound A-25

Same compound as Compound A-4 except $R^3$ is $C_2H_5$

Compound A-26

Same compound as Compound A-4 except $R^3$ is $CH_3OCH_2CH_2$

Compound A-27

Same compound as Compound A-4 except $R^3$ is $(CH_3)_2CH$

Compound A-28

Compound A-29

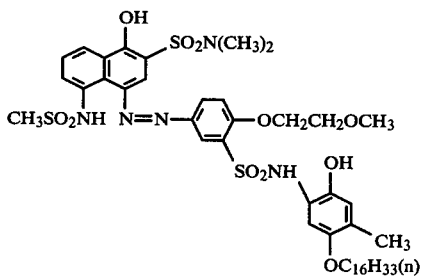

Compound A-30

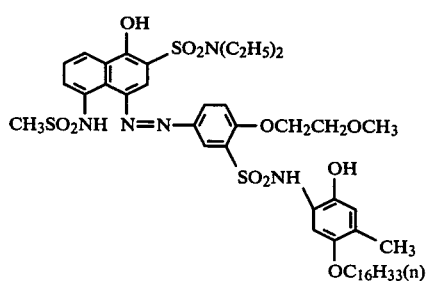

Compound A-31

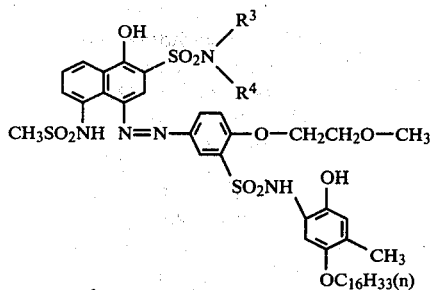

wherein $R^3$ is H and $R^4$ is cyclopentyl

Compound A-32

Same compound as Compound A-30 except $R^3$ is H and $R^4$ is

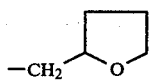

Compound A-34

Same compound as Compound A-30 except $R^3$ is H and $R^4$ is
—$CH_2$—$CH$=$CH_2$ Same compound as Compound A-30 except $R^3$ is H and $R^4$ is cyclohexyl

Compound A-33

Same compound as compound A-30 except $R^3$ is H and $R^4$ is

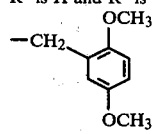

Compound A-35

Same compound as Compound A-30 except $R^3$ is H and $R^4$ is

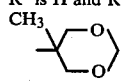

A dye releasing redox compound which is used in combination with the compound of the present invention can be incorporated into a layer containing the compound according to the present invention or into another layer. A dye releasing redox compound having an absorption in a longer wavelength region is preferably changed temporarily to a compound having an absorption in a short wavelength in a dispersion in view of color reproduction.

It is necessary that the image-receiving element used in this invention in combination with the above-described light-sensitive element contain an image-receiving mordanting layer comprising a mordant, such as the poly-4-vinylpyridine latex (in, preferably, polyvinyl alcohol) described in U.S. Pat. No. 3,148,061, the polyvinyl pyrrolidone described in U.S. Pat. No. 3,003,872, and the polymers containing quaternary ammonium salts as described in U.S. Pat. No. 3,239,337, individually or as a combination thereof. Also, the basic polymers described in U.S. Pat. Nos. 2,882,156, 3,625,694 and 3,709,690 can be effectively used as the mordant for the image-receiving layer. Other examples of mordants which can be effectively used in this invention are described in U.S. Pat. Nos. 2,484,430, 3,271,147, 3,184,309, etc.

Preferably the light-sensitive sheet of this invention is capable of neutralizing the alkali carried in from the alkaline processing composition. It is advantageous for this purpose for the light-sensitive sheet to include in a cover sheet or in an image-receiving element thereof a neutralizing layer containing an acid material in an amount sufficient to neutralize the alkali in the liquid processing composition, that is, containing an acid material at an area concentration higher than the equivalent of the alkali in the spread liquid processing composition. When a cover sheet having a neutralizing layer is used, the cover sheet can be superimposed on an image-receiving layer after such has been peeled from a light-sensitive element. Typical examples of preferred acid materials which can be used for this purpose are those described in U.S. Pat. Nos. 2,983,606, 2,584,030 and 3,362,819. The neutralizing layer may further contain a polymer such as cellulose nitrate, polyvinyl acetate, etc., and also the plasticizers as described in U.S. Pat. No. 3,557,237 in addition to the acid material. The acid material may be incorporated in the light-sensitive sheet in a microencapsulated form as described in German Patent Application (OLS) No. 2,038,254.

It is desirable that the neutralizing layer or the acid material-containing layer which can be used in this invention be separated from the spread layer of the liquid processing composition by a neutralization rate controlling layer (or timing layer). Gelatin, polyvinyl alcohol, or the compounds described in U.S. Pat. Nos. 3,455,686, 4,009,030 and 3,785,815, Japanese Patent Application Nos. 77946/75 and 90616/65, Japanese Patent Application (OPI) Nos. 92022/73, 64435/74, 22935/74 and 77333/76, Japanese Patent Publication Nos. 15756/69, 12676/71 and 41214/73, German Patent Application (OLS) Nos. 1,622,936, and 2,162,227, *Research Disclosure*, No. 151, 15162 (1967), etc., can be effectively used as the timing layer. The timing layer acts to retard the reduction in the pH of the liquid processing composition by the neutralizing layer until the desired development and transfer of dyes can be sufficiently accomplished.

The processing composition of the processing element used in this invention is a liquid composition containing the processing components necessary for developing silver halide emulsions and forming diffusion transfer dye images. The solvent of the processing composition is mainly water and contains, as the case may be, a hydrophilic solvent such as methanol, methyl Cellosolve, etc. The liquid processing composition contains alkali in an amount sufficient to maintain the necessary pH on developing the silver halide emulsion layers and for neutralizing acids (e.g., hydrohalic acids such as hydrobromic acid, etc., and carboxylic acids such as acetic acid, etc.) formed during development and dye image formation. Examples of suitable alkalis are hydroxides or salts of ammonium, alkali metals or alkaline earth metals or amines, such as lithium hydroxide, sodium hydroxide, potassium hydroxide, an aqueous dispersion of calcium hydroxide, tetramethylammonium hydroxide, sodium carbonate, trisodium phosphate, diethylamine, etc. It is desirable for the liquid processing composition to contain an alkaline material in a concentration such that the pH thereof can be maintained at above about 12, in particular, above 14 at room temperature. Further, preferably, the liquid processing composition contains a hydrophilic polymer such as high molecular weight polyvinyl alcohol, hydroxyethyl cellulose, sodium carboxymethyl cellulose, etc. These polymers contribute toward increasing the viscosity of the liquid processing composition above about 1 poise, preferably to 500 or 600 to 1,000 poises, at room temperature, which facilitates the uniform spreading of the processing composition at development as well as the formation of a non-fluid film when the aqueous medium has diffused into the photosensitive element and the image-receiving element during processing thereby concentrating the processing composition, which results in assisting unification of all of the elements after processing. The polymer film also contributes toward preventing coloring components from transferring into the image-receiving layer to stain the dye images formed after the formation of the diffusion transfer dye image is substantially completed.

As the case may be, it is advantageous for the liquid processing composition to further contain a light absorbing material such as $TiO_2$, carbon black a pH indicating dye, etc., or the desensitizer as described in U.S. Pat. No. 3,579,333 for preventing the silver halide emulsion layers from being fogged by ambient light during processing outside the camera. Furthermore, the liquid processing composition used in this invention may contain a development inhibitor such as benzotriazole.

It is preferred for the above-described processing composition to be retained in a rupturable container as described in U.S. Pat. Nos. 2,543,181, 2,643,886, 2,653,732, 2,723,051, 3,056,491, 3,056,492, 3,152,515, etc.

When the light-sensitive sheet of the present invention is a photographic film unit which has a construction such that after imagewise exposure, the processing of the film unit is performed by passing the film unit through a pair of juxtaposed pressure-applying members comprises:
(1) a support,
(2) a light-sensitive element as described above,
(3) an image-receiving element as described above,
(4) a processing element as described above, and
(5) a developing agent (which can be incorporated into the processing element or the light-sensitive element).

One embodiment of the film unit described above is disclosed in Belgian Patent 757,959. According to this embodiment, the film unit is prepared by coating on a transparent support an image-receiving layer, a substantially opaque light reflective layer in a face-to-face relationship. A rupturable container retaining an alkaline processing composition having incorporated therein an opacifying agent for light-intercepting such as, for example, carbon black, is disposed adjacent to and between the uppermost layer of the above-described light-sensitive element (protective layer) and the transparent cover sheet. The film unit is imagewise exposed in a camera through the transparent cover sheet and then the rupturable container retaining the alkaline processing composition is ruptured by the pressure-applying members when the film unit is withdrawn from the camera to spread uniformly the processing composition containing opacifying agent between the light-sensitive layer and the cover sheet, whereby the film unit is shielded from light in a sandwich form and development proceeds in a light place.

In these embodiments of film units, the neutralization mechanism as described above is preferably incorporated therein. In particular, the neutralizing layer is preferably positioned in the cover sheet and, further, the timing layer is positioned on the side toward where the processing solution is to be spread, if desired.

Moreover, other useful embodiments of the integral type of film units wherein the dye releasing redox compound of this invention can be used are described in, for example, U.S. Pat. Nos. 3,415,644, 3,415,645, 3,415,646, 3,647,487, and 3,635,707 and German Patent Application (OLS) No. 2,426,980.

The effects and advantages obtained according to the present invention are described below.

First, color images having less light-fading are obtained because of the superiority in the light fastness of the dyes released.

Second, color images with high quality are obtained when the dye releasing redox compound according to the present invention is used together with other redox compounds of good hue, since the hue of the dyes released is excellent and does not vary with changes of pH.

Third, the amount of dyes remaining at exposed areas in light-sensitive elements is very small, since the transferability of the dye released is excellent. Therefore, it is effective to obtain negative color images composed of the unreacted dye releasing redox compound which are obtained by stripping of the light-sensitive element and subjecting it to bleach processing (i.e., the negative can be easily used).

Fourth, the dyes released are hardly subjected to fading in a dark place due to a vinyl monomer such as acrylic acid or butyl acrylate which is present in a neutralizing layer.

EXAMPLE 1

Dye Compound A of the following formula:

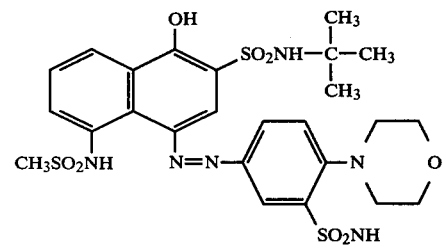

which is released from Compound 1 according to the present invention was dissolved in N,N-dimethylformamide (DMF) to prepare a $10^{-3}$ M solution. 0.25 ml of the solution was diluted with 11.5 ml of DMF and a mixture of 1.25 ml of a $10^{-1}$ M solution of butylacrylate and 12. 5 ml of a buffer having a pH of 5.05 (Britton-Robinson Buffer) was added thereto. The solution was allowed to stand at room temperature (25° to 29° C.) and the decrease of absorbance at a maximum absorption wavelength in a visible region was measured. From the values measured the remaining rate of Dye Compound A was determined and assuming that the decrease of dye A can be shown by a pseudo first order equation, a reaction rate constant of the pseudo first order reaction, i.e., k was determined.

In a similar manner, k was determined with respect to Dye Compounds B, C and D released from Compounds 5, 7 and 10, respectively.

Also, k was determined in a similar manner with respect to Dye Compound E described in Japanese Patent Application (OPI) No. 115528/75 for comparison with the above compounds. The results obtained are shown in Table 1.

TABLE 1

Reaction of Released Dye Compound with Butyl Acrylate

| Compound | $R^{12}$ | $R^{13}$ | $R^{14}$ | k (day$^{-1}$) |
|---|---|---|---|---|
| A | H | —N(morpholino) | —SO$_2$NH$_2$ | $4.5 \times 10^{-2}$ |
| B | —N(morpholino) | H | —SO$_2$NH$_2$ | $3.9 \times 10^{-2}$ |
| C | —N(C$_2$H$_4$OCH$_3$)$_2$ | H | —SO$_2$NH$_2$ | $5.1 \times 10^{-2}$ |
| D | H | —N(pyrrolidino) | —SO$_2$NH$_2$ | $1.1 \times 10^{-2}$ |
| E | H | —SO$_2$NH$_2$ | H | $9.8 \times 10^{-2}$ |

It is apparent from the results shown in Table 1 that the reaction rate constant k of Dye Compounds, A, B, C and D released from the compounds according to the present invention with butyl acrylate is extremely small in comparison with that of Comparison Compound E. Similar results were obtained with respect to the dye compounds released from the compounds represented by the general formula (I). These experimental results are corresponding to results of fading in a dark of transferred images in a practical photographic system and it is apparent that the durability of color images in a dark place is remarkably improved due to the presence of the amino group of —N'R$^1$R$^2$.

EXAMPLE 2

On a polyethylene terephthalate transparent support were coated the layers described below in the order listed to prepare a photographic light-sensitive sheet.

(1) A mordanting layer containing 3.0 g/m$^2$ of a mordant shown below:

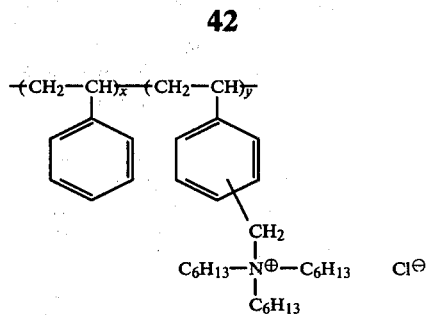

x:y = 50:50 and 3.0 g/m$^2$ of gelatin.

(2) A white light reflective layer containing 20 g/m$^2$ of titanium oxide and 2.0 g/m$^2$ of gelatin.

(3) A light-shielding layer containing 2.7 g/m$^2$ of carbon black and 2.7 g/m$^2$ of gelatin.

(4) A layer containing 0.8 g/m$^2$ of the magenta dye releasing redox compound according to the present invention, 0.2 g/m$^2$ of diethyllaurylamide and 1.20 g/m$^2$ of gelatin.

(5) A layer containing a green-sensitive internal latent image type direct reversal silver iodobromide emulsion (halogen composition in the silver halide: 1 mol% of iodide; silver amount: 2.0 g/m$^2$; gelatin: 1.5 g/m$^2$), 0.08 mg/m$^2$ of a fogging agent represented by the following formula:

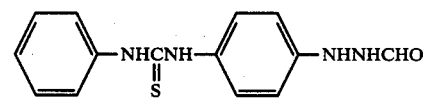

and 0.18 g/m$^2$ of sodium 5-pentadecylhydroquinone-2-sulfonate.

(6) A layer containing 0.94 g/m² of gelatin.

Also, the processing solution and a cover sheet shown below were prepared.

| Processing Solution: | | |
|---|---|---|
| 1-Phenyl-4-methyl-4-hydroxymethyl-3-pyrazolidone | 10 | g |
| Methylhydroquinone | 0.18 | g |
| 5-Methylbenzotriazole | 4.0 | g |
| Sodium Sulfite (anhydrous) | 1.0 | g |
| Carboxymethyl Cellulose Na Salt | 40.0 | g |
| Benzyl Alcohol | 1.5 | ml |
| Carbon Black | 150 | g |
| Potassium Hydroxide (28% aq. soln.) | 200 | cc |
| H₂O | 550 | cc |

The processing solution of the above composition was filled into a container rupturable with pressure by 0.8 g each.

Cover Sheet

On a polyethylene terephthalate transparent support were coated a neutralizing acid polymer layer containing 15 g/m² of polyacrylic acid (a 10 wt% aqueous solution having viscosity of about 1,000 cp) and a neutralizing timing layer containing 3.8 g/m² of acetyl cellulose (hydrolysis of 100 g of acetyl cellulose forms 39.4 g of acetyl groups), and 0.2 g/m² of a styrene/maleic anhydride copolymer (composition ratio: styrene: maleic anhydride=about 60:40; molecular weight: about 50,000) to prepare a cover sheet.

The above-described cover sheet was superimposed on the above-described light-sensitive sheet. Exposure was performed through a wedge having stepwise different density from the cover sheet side. Then, the processing solution described above was spread between both sheets in a thickness of 85 microns (the spreading was performed with assistance of a pressure roller). The processing was carried out at 25° C. After processing, the transferred images were observed through the transparent support of the light-sensitive sheet. The maximum density and the minimum density of the magenta transferred images formed were measured 1 hour after the processing. Further, the remaining ratio of magenta color image after allowing to stand the film unit thus-processed for 7 days at 80° C. and 60% relative humidity (fading in a dark place) and the remaining ratio of magenta color image after exposed the film unit thus processed to a light of 17,000 lux for 5 days using a fluorescent lamp fading tester (light-fading) were determined. The results thus-obtained are shown in Table 2.

TABLE 2

| Dye Releasing Redox Compound | Maximum Density | Minimum Density | Fading in a Dark | Light Fading |
|---|---|---|---|---|
| Compound 1 of this invention | 1.89 | 0.26 | 77 | 98 |
| Comparison* | 2.08 | 0.26 | 54 | 95 |

*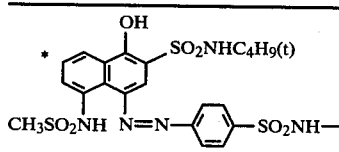
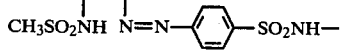

TABLE 2-continued

| Dye Releasing Redox Compound | Maximum Density | Minimum Density | Fading in a Dark | Light Fading |
|---|---|---|---|---|

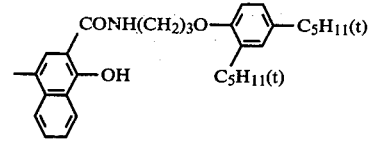

It is apparent from the results shown in Table 2 that when the redox compound according to the present invention is used, the fading of the color image in a dark place is extremely small in comparison with using the conventional redox compound.

While the invention has been described in detail and with reference to specific embodiments thereof, it will be apparent to one skilled in the art that various changes and modifications can be made therein without departing from the spirit and scope thereof.

What is claimed is:

1. A photographic light-sensitive sheet for the color diffusion transfer process which comprises a support having thereon at least one light-sensitive silver halide emulsion layer having associated therewith a compound represented by the following general formula (I):

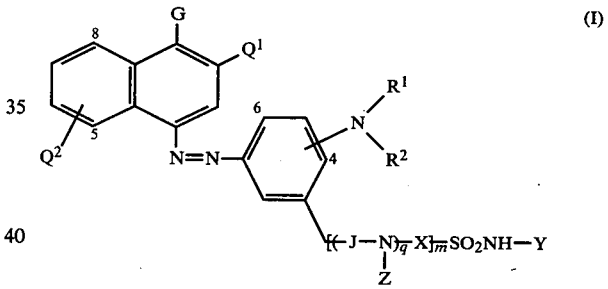

wherein
Q¹ represents a hydrogen atom; a halogen atom; a sulfamoyl group represented by the formula —SO₂NR³R⁴ wherein R³ represents a hydrogen atom or an alkyl group, R⁴ represents a hydrogen atom or an R⁴ᵃ group wherein R⁴ᵃ represents an alkyl group, an aralkyl group or a phenyl group, and R³ and R⁴ may combine directly or through an oxygen atom to form a ring; a group represented by the formula —SO₂R⁵ wherein R⁵ represents an alkyl group or an aralkyl group; a carboxy group; a group represented by the formula —COOR⁶ wherein R⁶ represents an alkyl group or a phenyl group; or a group represented by the formula —CONR³R⁴ wherein R³ and R⁴ each has the same meaning as defined above;

Q² is positioned at the 5- or the 8-position to the hydroxy group and represents a hydroxy group, a group represented by the formula —NHCOR⁴ᵃ or a group represented by the formula —NHSO₂R⁴ᵃ wherein R⁴ᵃ has the same meaning as defined above;

G represents a hydroxyl group, a salt thereof, or a hydrolyzable acyloxy group represented by the formula

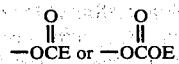

wherein E represents an alkyl group or a phenyl group;

$R^1$ and $R^2$, which may be the same or different, each represents an alkyl group; and $R^1$ and $R^2$ may combine with each other and represent an atomic group necessary to form a 5-membered or 6-membered heterocyclic ring;

m and q each represents 0 or 1;

J represents a sulfonyl group or a carbonyl group;

Z represents a hydrogen atom or an alkyl group;

X represents a divalent bonding group represented by the formula $-A^1-L_n\!\!-\!\!(A^2)\!\!-\!\!_p$ wherein $A^1$ and $A^2$, which may be the same or different, each represents an alkylene group, an aralkylene group, a phenylene group or a substituted phenylene group; L represents a divalent group selected from the group consisting of an oxy group, a carbonyl group, a carboxyamido group, a carbamoyl group, a sulfonamido group, a sulfamoyl group, a sulfinyl group and a sulfonyl group, and p and n each represents 0 or 1; and the group represented by the formula $Y-NHSO_2-$ is a redox center which functions to release a diffusible dye as a result of self cleavage due to oxidation with Y representing a carboxylic ring containing at least one unsaturated double bond and a ballast group and substituted with (a) a hydroxy group or a precursor thereof or (b) an amino group, the substitution of said hydroxy group or said amino group being at the position ortho or para to the $SO_2NH-$ group.

2. The photographic light-sensitive sheet of claim 1, wherein said amino group $NR^1R^2$ is positioned at the 4- or 6-position to the azo group.

3. The photographic light-sensitive sheet of claim 1, wherein said alkyl group represented by $R^1$ or $R^2$ is an alkyl group having 1 to 6 carbon atoms.

4. The photographic light-sensitive sheet of claim 1, wherein said alkyl group is a substituted alkyl group having 1 to 10 carbon atoms and is substituted with an alkoxy group or a halogen atom.

5. The photographic light-sensitive sheet of claim 1, wherein said sulfamoyl group represented by $Q^1$ is a sulfamoyl group represented by the formula $-SO_2NR^3R^4$ wherein $R^3$ is a hydrogen atom or an alkyl group having 1 to 8 carbon atoms, $R^4$ and represents a hydrogen atom, an alkyl group having 1 to 8 carbon atoms, an aralkyl group, a phenyl group or a substituted phenyl group having 6 to 9 carbon atoms.

6. The photographic light-sensitive sheet of claim 5, wherein said $R^3$ and $R^4$ each represents a hydrogen atom.

7. The photographic light-sensitive sheet of claim 5, wherein one of said $R^3$ and $R^4$ represents a hydrogen atom and the other of said $R^3$ and $R^4$ represents an alkyl group having 1 to 4 carbon atoms.

8. The photographic light-sensitive sheet of claim 1, wherein said m is 0.

9. The photographic light-sensitive sheet of claim 1, wherein said $Y-NHSO_2-$ is a sulfamoyl group represented by the following formula:

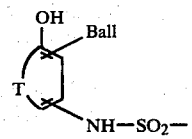

wherein Ball represents a ballast group; T represents the carbon atoms necessary to complete a benzene ring, which may be unsubstituted or substituted, or a naphthalene ring, which may be a unsubstituted or substituted; the $NHSO_2-$ group is present at the o- or p-position to the hydroxy group; and when T represents the atoms necessary to complete a naphthalene ring, Ball can be bonded to either of the two rings.

10. The photographic light-sensitive sheet of claim 9, wherein said ballast group contains a hydrophobic residue having 8 to 32 carbon atoms.

11. The photographic light-sensitive sheet of claim 9, wherein said ballast group is represented by the following formulae:

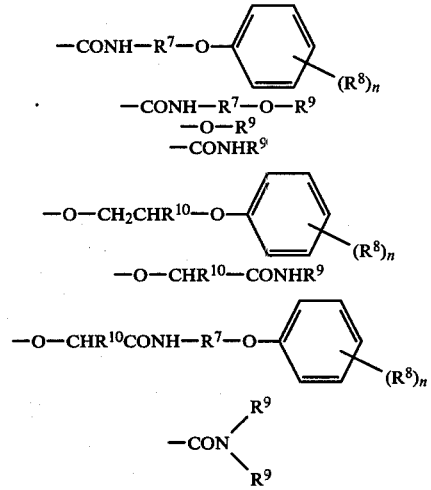

wherein $R^7$ represents an alkylene group having 1 to 10 carbon atoms, $R^8$ represents a hydrogen atom or an alkyl group having 1 to 10 carbon atoms, n represents an integer of 1 to 5, $R^9$ represents an alkyl group having 4 to 30 carbon atoms and in the formula

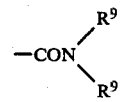

the $R^9$'s may be the same or different, and $R^{10}$ represents an alkyl group having 1 to 8 carbon atoms.

12. The photographic light-sensitive sheet of claim 9, wherein $R^1$ and $R^2$ combine to form a pyrrolidine ring or a morpholine ring, or $R^1$ represents $-CH_2CH_2-O-CH_3$ and $R^2$ represents an alkyl group having 1 to 4 carbon atoms; $Q^1$ represents a sulfamoyl group represented by the formula $-SO_2NR^3R^4$ wherein $R^3$ and $R^4$, which may be the same or different, each represents a hydrogen atom or an alkyl group having 1 to 4 carbon atoms or $R^3$ and $R^4$ combine directly or through an oxygen atom to form a 5- or 6-membered ring; $Q^2$ represents a hydroxy group positioned at the 5- or 8- position to G or a group represented by the formula —NHSO$_2$R$^{4a}$ wherein R$^{4a}$ is an alkyl group having 1 to 4 carbon atoms positioned at the 5-position to G; and m is 0.

13. The photographic light-sensitive sheet of claim 1, wherein the amino group —NR$^1$R$^2$ is positioned at the 4-position to the azo group; R$^1$ and R$^2$ are bonded to each other to form a pyrrolidine ring or a morpholine ring; Q$^1$ is a sulfamoyl group represented by the formula —SO$_2$NR$^3$R$^4$ wherein R$^3$ represents a hydrogen atom and R$^4$ represents a tertbutyl group or an isopropyl group; Q$^2$ represents a group represented by the formula —NHSO$_2$R$^{4a}$ wherein R$^{4a}$ is a methyl group at the 5-position to G, m is O and Y represents an o-hydroxyphenylsulfamoyl group having an alkyl group at the meta position to the hydroxy group in addition to a ballast group.

* * * * *